(12) United States Patent
Singh et al.

(10) Patent No.: US 10,231,991 B2
(45) Date of Patent: *Mar. 19, 2019

(54) BIOMATERIALS COMPRISING HYALURONIC ACID BINDING PEPTIDES AND EXTRACELLULAR MATRIX BINDING PEPTIDES FOR HYALURONIC ACID RETENTION AND TISSUE ENGINEERING APPLICATIONS

(71) Applicant: THE JOHNS HOPKINS UNIVERSITY, Baltimore, MD (US)

(72) Inventors: Anirudha Singh, Baltimore, MD (US); Shimon Unterman, Brookline, MA (US); Michael Corvelli, Baltimore, MD (US); Jennifer Elisseeff, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/906,111

(22) PCT Filed: Jul. 16, 2014

(86) PCT No.: PCT/US2014/046796
§ 371 (c)(1),
(2) Date: Jan. 19, 2016

(87) PCT Pub. No.: WO2015/009787
PCT Pub. Date: Jan. 22, 2015

(65) Prior Publication Data
US 2016/0158270 A1 Jun. 9, 2016

Related U.S. Application Data

(60) Provisional application No. 61/856,167, filed on Jul. 19, 2013.

(51) Int. Cl.
*A61K 9/00* (2006.01)
*C08L 5/08* (2006.01)
(Continued)

(52) U.S. Cl.
CPC .......... *A61K 31/728* (2013.01); *A61K 9/0019* (2013.01); *A61K 9/0048* (2013.01);
(Continued)

(58) Field of Classification Search
None
See application file for complete search history.

(56) References Cited

U.S. PATENT DOCUMENTS

| | | |
|---|---|---|
| 5,589,466 A | 12/1996 | Felgner et al. |
| 2005/0159343 A1 | 7/2005 | Takashima et al. |
| 2011/0269231 A1 | 11/2011 | Murphy et al. |

FOREIGN PATENT DOCUMENTS

| | | |
|---|---|---|
| WO | 2006130974 A1 | 12/2006 |
| WO | 2008-063291 A2 | 5/2008 |

(Continued)

OTHER PUBLICATIONS https://en.wikipedia.org/wiki/Poloxamer_407, accessed Jul. 27, 2017.*
(Continued)

*Primary Examiner* — Elizabeth C. Kemmerer
(74) *Attorney, Agent, or Firm* — John Hopkins Technology Ventures

(57) ABSTRACT

The present invention provides novel biomaterial compositions and methods having a technology to improve retention of hyaluronic acid (HA). The biomaterial compositions utilize small HA binding peptides and extracellular matrix binding (ECM) peptides that are tethered to synthetic biocompatible polymers. When tethered to the polymers, the peptide region allows the polymers to bind to HA and to tissues such as cartilage. The novel biomaterial composi-
(Continued)

tions can be used to coat or chemically modify cartilage or tissues with a biologically compatible polymer having HA binding peptides, which allow HA to bind to the surface of the cartilage or tissues. Methods of using same are also provided.

13 Claims, 9 Drawing Sheets

Specification includes a Sequence Listing.

(51) Int. Cl.
    A61K 38/08    (2006.01)
    A61K 38/10    (2006.01)
    A61K 47/60    (2017.01)
    A61K 47/69    (2017.01)
    A61L 27/20    (2006.01)
    A61L 27/22    (2006.01)
    A61K 31/728    (2006.01)

(52) U.S. Cl.
CPC .............. *A61K 38/08* (2013.01); *A61K 38/10* (2013.01); *A61K 47/60* (2017.08); *A61K 47/6957* (2017.08); *A61L 27/20* (2013.01); *A61L 27/227* (2013.01); *A61L 2400/10* (2013.01); *A61L 2400/18* (2013.01); *A61L 2430/06* (2013.01); *A61L 2430/16* (2013.01)

(56) References Cited

FOREIGN PATENT DOCUMENTS

WO    2008063291 A2    5/2008
WO    2013110056 A1    7/2013

OTHER PUBLICATIONS

Briscoe, W. H. et al. Boundary lubrication under water. Nature 444, 191-194, doi:10.1038/nature05196 (2006).
Chen, M., et al. Lubrication at physiological pressures by polyzwitterionic brushes. Science 323, 1698-1701, doi:10.1126/science.1169399 (2009).
Greene, et al. Adaptive mechanically controlled lubrication mechanism found in articular joints. (2011) PNAS 108, 13: 5255-5259.
Jackson, D. W., et al. Intra-articular distribution and residence time of Hylan A and B: a study in the goat knee. Osteoarthritis Cartilage 14, 1248-1257, doi:10.1016/j.joca.2006.05.015 (2006).
Jones, A., et al. Binding and Localization of Recombinant Lubricin to Articular Cartilage Surfaces. (2006) Ortho Res DOI 10.1002/jor.20325.
Julovi S., et al. Inhibition of interleukin-1betastimulated production of matrix metalloproteinases by hyaluronan via CD44 in human articular cartilage. Arthritis and rheumatism 50, 516-525, doi:10.1002/art.20004 (2004).
Moghani, T., et al. Determinants of friction in soft elastohydrodynamic lubrication. J Biomech 42, 1069-1074, doi:10.1016/j.jbiomech.2009.02.021 (2009).
Morrell, K. C., et al. Corroboration of in vivo cartilage pressures with implications for synovial joint tribology and osteoarthritis causation. Proceedings of the National Academy of Sciences of the United States of America 102, 14819-14824, doi:10.1073/pnas.0507117102 (2005).
Mummert, M. E., et al. Development of a peptide inhibitor of hyaluronan-mediated leukocyte trafficking. J Exp Med 192, 769-779 (2000).
Neu, C. P., et al. The interface of functional biotribology and regenerative medicine in synovial joints. Tissue engineering. Part B, Reviews 14, 235-247, doi:10.1089/ten.teb.2008.0047 (2008).
Presti, D., et al. Hyaluronan-mediated protective effect against cell damage caused by enzymatically produced hydroxyl (OH.) radicals is dependent on hyaluronan molecular mass. Cell Biochem Funct 12, 281-288, doi:10.1002/cbf.290120409 (1994).
Schmidt, T. A., et al. Boundary lubrication of articular cartilage: role of synovial fluid constituents. Arthritis and rheumatism 56, 882-891, doi:10.1002/art.22446 (2007).
Schmidt, T. A., et al. Effect of synovial fluid on boundary lubrication of articular cartilage. Osteoarthritis Cartilage 15, 35-47, doi:10.1016/j.joca.2006.06.005 (2007).
Stafford, C. T., et al. Studies on the Concentration and Intrinsic Viscosity of Hyaluronic Acid in Synovial Fluids of Patients with Rheumatic Diseases. Ann Rheum Dis 23, 152-157 (1964).
Zhang, W. et al. OARSI recommendations for the management of hip and knee osteoarthritis: part III: Changes in evidence following systematic cumulative update of research published through Jan. 2009. Osteoarthritis Cartilage 18, 476-499, doi:10.1016/j.joca.2010.01.013 (2010).
Zmolik, J. M., et al. Pep-1 as a novel probe for the in situ detection of hyaluronan. J Histochem Cytochem 53, 745-751, doi:10.1369/jhc.4A6491.2005 (2005).
Extended European search report dated Nov. 18, 2016, for EP application 14825803.1.
Ali, M., et al., "Controlled release of high molecular weight hyaluronic acid from molecularly imprinted hydrogen contact lenses" Pharmaceutical Research (2009) vol. 26, No. 3.
Mummert, M, "Development of a peptide inhibitor of hyaluronan-mediated leukocyte trafficking" J. Exp. Med., Sep. 18, 2000, vol. 192, No. 6, pp. 769-779.
Oh, E., et al., "Target specific and long-acting delivery of protein, peptide, and nucleotide therapeutics using hyaluronic acid derivatives" Journal of Controlled Release (2010) vol. 141, pp. 2-12.

\* cited by examiner ized and often abnormal joint motion. All of these contribute to a much greater reliance on boundary lubrication at the same time that many boundary lubricants are depleted and disrupted by inflammatory processes. The resultant higher friction leads to pain, accelerated degeneration of cartilage, and disease progression. HA is believed to improve joint lubrication through its viscoelastic properties at high molecular weights, although biological functions may also play a role. As a result, one common clinical treatment for OA is injection of HA directly into the joint to improve synovial lubrication. Despite the physical and biological attributes of HA, clinical results of HA injections have been inconclusive and suspect due to the clearly observable rapid turnover of HA molecules within the joint after injection and limited ability to target areas where increased lubrication is needed. Alternative approaches to improving joint health and lubrication are investigating the other synovial fluid components, lubricin and surface active phospholipids. Despite the drastic degenerative changes in the tissue surface with OA and the critical role the surface plays in lubrication, there has been no attempt to target the cartilage surface to improve joint lubrication and overall joint health. In fact, the tissue surface is an ideal focus for therapeutic intervention as it is more stable than the constantly circulating synovial fluid and may be better suited to protect the underlying tissue from exposure to physical and biological elements. Hence, the duration of an enhancement/repair/treatment achieved with hydrogel compositions is limited in time, and frequently requires the recipient to undergo additional and expensive repeat injections/treatments to maintain a desired effect.

BIOMATERIALS COMPRISING HYALURONIC ACID BINDING PEPTIDES AND EXTRACELLULAR MATRIX BINDING PEPTIDES FOR HYALURONIC ACID RETENTION AND TISSUE ENGINEERING APPLICATIONS

CROSS-REFERENCE TO RELATED APPLICATIONS

This application is a 35 U.S.C. § 371 U.S. national entry of International Application PCT/US2014/046796, having an international filing date of Jul. 16, 2014, which claims the benefit of U.S. Provisional Application No. 61/856,167, filed Jul. 19, 2013, the content of each of the aforementioned applications is herein incorporated by reference in their entirety.

STATEMENT OF GOVERNMENTAL INTEREST

This invention was made with government support under grant no. AG328232 awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jul. 19, 2013, is named P12599-01_ST25.txt and is 2,021 bytes in size.

BACKGROUND OF THE INVENTION

Tissue lubrication is crucial for the normal function of articulating joints, eyes, and lungs. Compromised lubrication is a hallmark of disease in these organ systems, warranting investigation into therapeutic strategies to restore function. Current clinical strategies using injections or eye drops to deliver lubricating biopolymers such as hyaluronic acid (HA) to the diseased tissue are largely ineffective because the lubricant is quickly cleared.

Lubrication is key to a number of industrial technologies, including car engines, wind turbines, and hard drives, where chemists work together with engineers to design surfaces that work together with liquid lubricants to achieve low-friction systems. Lubrication in tissues is also important to maintain a low-friction movement within a number of biological systems, including the pleural cavity, the surface of the eye, and diarthroidal joints. Medical devices employed in these tissues generally lack lubrication, hampering their tissue replacement function. In diarthroidal joints, healthy painless movement is facilitated by both molecules at the tissue surface and in the lubricating synovial fluid. Synovial fluid bathes the joint surface with several molecules that contribute to boundary lubrication, including lubricin, surface-active phospholipids, and hyaluronic acid (HA). The role of each of these components has been supported and challenged on the basis of various in vitro studies on cartilage lubrication, however in a healthy joint these molecules work together synergistically to reduce friction coefficients in boundary lubrication to achieve normal physiological performance. Today, therapeutic options to enhance tissue lubrication focus only on replacing or enhancing the lubricant in the fluid phase.

The breakdown of joint lubrication is a major hallmark of osteoarthritis (OA), stimulating significant interest in understanding and enhancing joint lubrication to improve overall joint health. Only about 10% of the cartilage surface area comes into direct contact with the opposite surface during walking in the healthy knee, suggesting the role of boundary lubrication is relatively small. Osteoarthritic knees are further challenged by narrow intra-articular spaces, roughened cartilage surfaces, and often abnormal joint motion.

A need continues to exist in the tissue repair and reconstructive arts for improved HA containing biomaterial compositions which improve retention of HA in the hydrogel and are longer lasting.

SUMMARY OF THE INVENTION

The present invention provides a transformational biomaterials approach to engineering lubrication at the tissue surface. In accordance with some embodiments, articular cartilage explants were modified with a synthetic peptide-polymer system designed to non-covalently bind HA to the tissue surface and work synergistically with HA in the local fluid environment. Lubrication properties of chemically-modified tissue surfaces with bound HA were similar to those of native tissue bathed in HA lubricant. Biomaterials-mediated strategies that locally concentrate HA and create a self-healing coating of biological lubricant on tissue surfaces provide physical and biological benefits to treat tissue-lubricating dysfunction.

In accordance with some embodiments, the present inventors developed a strategy to modify tissue surfaces with biomaterials to transform the fluid interface and improve lubrication (FIG. 1). The technology was first applied to cartilage tissue (FIG. 1a). An HA-binding peptide (HAB-Pep), discovered through phage display, was covalently bound to the cartilage surface via a heterobifunctional poly(ethylene glycol) (PEG) chain (FIG. 1b). The HA-binding peptide-polymer therapy was designed to noncovalently bind HA (endogenously produced or exogenously injected) to the tissue surface (FIG. 1b). This technology is the subject of International Patent Application No. PCT/US2013/022502, and incorporated by reference in its entirety.

The present inventors hypothesized that localizing HA to the surface of articular cartilage would enhance the boundary lubrication effects of HA in the synovial fluid and mimic the presumed role of lubricin to improve joint lubrication in a healthy knee. In addition, HA has a number of biological functions that would be ideal to concentrate at the tissue surface including reducing inflammation, mediating matrix metalloproteinase expression and protecting cells from radical damage. Coating the surface with HA can also physically protect the cartilage surface from cytokines and degrading enzymes that are frequently found in a diseased or post-traumatic joint. Finally, and most critically, the presence of the polymer-HA binding modification provides a mechanism to concentrate HA on a tissue surface. Numerous endogenous enzymes can degrade HA and its fluid concentrations can quickly decrease with normal turn over. The HABPep can recapture HA that is lost through a physical or biological mechanism and provide the stable anchor on the tissue surface that is necessary to dynamically bind and concentrate HA where it is needed.

Therefore, in accordance with an embodiment, the present invention provides a biomaterial comprising at least one biologically compatible polymer having one or more HA binding peptides (HABPep) covalently linked to the biologically compatible polymer, and one or more extracellular matrix binding peptides (ECMBPep) covalently linked to the biologically compatible polymer.

In accordance with an embodiment, the present invention provides a method of treating a cartilage defect in a tissue of a subject comprising administering to the tissue of the subject in need of treatment, a therapeutically effective amount of the biomaterial compositions described herein.

In accordance with another embodiment, the present invention provides a method of treating osteoarthritis in a tissue of a subject comprising administering to the tissue of the subject in need of treatment, a therapeutically effective amount of the biomaterial compositions described herein.

In accordance with still another embodiment, the present invention provides a method of coating the pleural cavity of a subject comprising administering to the pleural cavity of the subject in need of treatment, a therapeutically effective amount of the biomaterial compositions described herein.

In accordance with a further embodiment, the present invention provides a therapeutic method for the treatment of eye diseases by means of an eye surgery treatment, comprising applying to the eye of a subject in need of such treatment a therapeutically effective amount of the biomaterial compositions described herein.

In accordance with still another embodiment, the present invention provides a therapeutic method for the treatment of dry eye in a subject comprising applying to the eye of a subject in need of such treatment a therapeutically effective amount of the biomaterial compositions described herein.

In accordance with an embodiment, the present invention provides a method for making the biomaterial compositions described herein, comprising: a) obtaining a sufficient amount of one or more biocompatible polymers conjugated to at least one or more N-succinimide groups and one or more maleimide groups in a suitable solution; b) adding to the solution of a) a sufficient amount of one or more ECMBPep and allowing it to react with the one or more N-succinimide groups to produce one or more biocompatible polymers having one or more ECMBPep which are covalently linked to the biocompatible polymers; c) obtaining a sufficient amount of having one or more thiolated HA binding peptides (C-HABPep) in a suitable solution; d) adding the solution of b) to the solution of c) and mixing for a sufficient period of time to produce one or more biocompatible polymers having one or more HA binding peptides (HABPep) which are covalently linked to the biocompatible polymers which are covalently linked to one or more ECMBPep; e) adding to the solution of d) a sufficient amount of hyaluronic acid (HA) in a suitable solvent for a sufficient time to allow HA to bind to the HABPep in the solution; f) removing the unreacted reagents of b), c) and e) and purifying the remaining product.

DETAILED DESCRIPTION OF THE INVENTION

Figure 1:
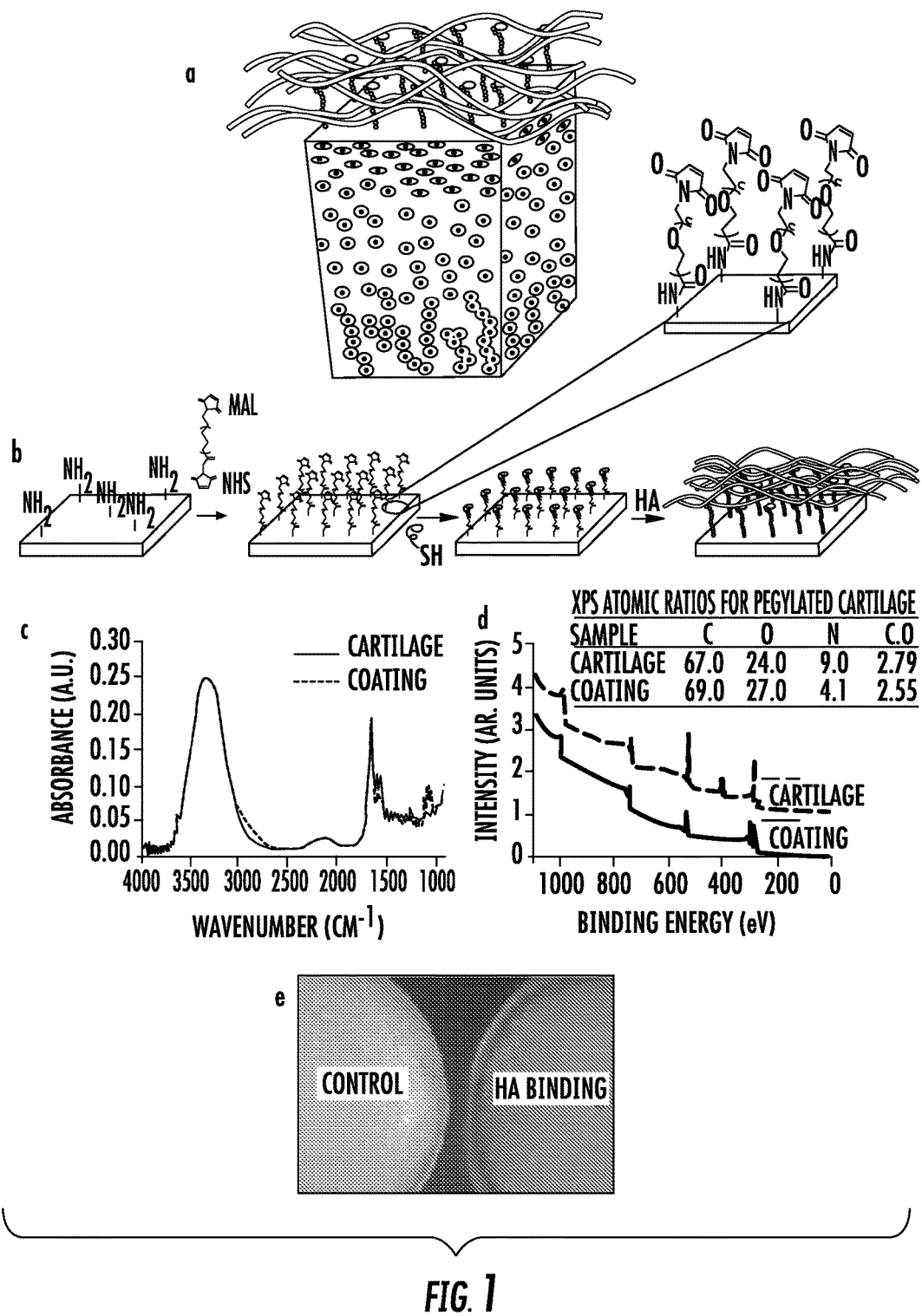
FIG. 1 depicts tissue surface modification with an HA binding polymer system. 1a, Schematic of cartilage surface modified with an HABpep designed to interact with and bind HA in surrounding fluid. 1b, An in vitro covalent strategy for coating the cartilage surface with MAL-PEG-NHS crosslinker, which, on reaction with primary amines of the cartilage surface, creates an exposed thiol-reactive surface. Subsequently, a thiolated HABpep is reacted to the maleimide functionality. On exposure to an HA solution, the HA binds to the peptide-polymer coating on the cartilage surface. 1c, The PEG crosslinker reaction to articular cartilage was confirmed by ATR-FTIR spectroscopy that validated the presence of the ether-rich PEG coating with a large ether peak at ~1066 $cm^{-1}$. 1d, PEGylation was further verified by XPS atomic ratios. Compared to unmodified cartilage, coated samples had a carbon to oxygen ratio closer to 2, the ratio in PEG, and significantly lower nitrogen content. 1e, HA-binding functionality of the peptide-conjugated cartilage was visualized using a biotinylated HA. Biotinylated HA was synthesized and applied to unmodified cartilage and cartilage modified with the HA-binding polymer system. After thorough washing, the biotinylated HA was treated with streptavidin and horseradish peroxidase for visualization. The tissue surfaces treated with the HA-binding polymer coating stained darker than the untreated native cartilage.

Biomaterials such as hydrogels based on natural polymers, such as alginate, collagen and hyaluronic acid (HA), are widely used for tissue engineering applications.

In accordance with an embodiment, the present invention provides novel biomaterial compositions which bind to tissue surfaces and bind HA. The embodiments of the present invention provide biomaterials that allow tissue modification with HA binding polymer coatings, and utilizes a synthetic peptide to target and locally concentrate hyaluronic acid to tissue surfaces. The present inventive biomaterials were applied to articular cartilage surfaces to work synergistically with biopolymers in the synovial fluid to improve tissue lubrication. While improving boundary lubrication of osteoarthritic cartilage is unlikely to reverse the degeneration of the joint, it can help slow the wear processes in a damaged joint and potentially reduce pain. Post-traumatic injuries that result in a destabilized knee and/or focal cartilage defects often lead to a joint with a compromised mechanical environment that play a role in initiating osteoarthritic. Prophylactic treatment with HA-binding biomaterials as coatings during trauma treatment can enhance local boundary lubrication and prevent or reduce the onset of joint degeneration. This HA-binding biomaterial can be a powerful tool for effective modification of the lubrication environment of the knee and for other tissues where lubrication or the presence of HA is critical for homeostasis and health.

As used herein, "biocompatible biomaterial" are materials that can be used for tissue reconstruction or cosmetic procedures that are acceptable for use in a mammal, preferably in a human subject.

By way of example, and not limitation, and in particular embodiments, the polymer can comprise synthetic reactants and comprises poly(ethylene glycol) (PEG) or a derivative thereof.

In accordance with an embodiment, the biocompatible polymer can be PEG or a derivative thereof.

In accordance with a further embodiment, the biocompatible polymer can be hydrophilic.

In accordance with still another embodiment, the biocompatible polymers are selected from the group consisting of: Poly(ethylene glycol), Poly(propylene glycol), Poly(methyl vinyl ether), Oligoethylene, Poly(isobutylene) Poly(tetrahydrofuran) Poly(oxytrimethylene), Poly(dimethylsiloxsane), Poly(dimethylsilane), Nylon 6, Nylon 11, Poly(acrylonitrile), Squalane, Poly(1,3-dioxolane), Poly(iminooligomethylene), Poly(l-lysine), Polyethyleneimine, Poly(adipate), Poly(l-caprolactone), Poly(L-lactic acid), or derivatives thereof.

In accordance with an embodiment, the HABPep is a peptide which is capable of specifically binding HA. Many such HA binding peptides are known in the art. See for example WO/2006/130974, which describes many such peptides which have at least one repetition of the amino acid residue sequence $B_1X_7$-$B_2$ where B is any basic amino acid residue and $X_7$ are any 7 non-acidic amino acid residues. The binding of the peptide to HA may be enhanced by the addition of basic amino acid residues between B1 and B2 or flanking either end of motif (non-conservative substitutions).

The HABP52 family of HA binding peptides includes peptides with an amino acid sequence selected from the group consisting of i) (RRDDGAHWQFNALTVR) (SEQ ID NO: 1) or (CRRDDGAHWQFNALTVR) (SEQ ID NO: 2) or a conservative amino acid substitution thereof at a residue position other than 4, 5, 6, 9, 10 or 11, ii) Gly-Ala-Ala-Trp-Gln-Phe-Asn-Ala-Leu-Thr-Val-Arg (SEQ ID NO: 9) or a conservative amino acid substitution thereof at a residue position other than 4, 5, 6, 9, 10 or 11, iii) Gly-Ala-His-Trp-Gln-Phe-Ala-Ala-Leu-Thr-Val-Arg (SEQ ID NO: 10) or a conservative amino acid substitution thereof at a residue position other than 4, 5, 6, 9, 10 or 11, and iv) Gly-Ala-His-Trp-Gln-Phe-Asn-Ala-Leu-Thr-Val-Ala (SEQ ID NO: 11) or a conservative amino acid substitution thereof at a residue position other than 4, 5, 6, 9, 10 or 11.

As used herein, the term "extracellular matrix binding peptide (ECMBPep)" means a protein, peptide or fragment which is capable of specifically binding extracellular matrix proteins, such as collagen I or collagen II. For example, in an embodiment, the ECMBPep for collagen I is: YSFYSDESLQ (SEQ ID NO: 3), and for collagen II is: WYRGRL (SEQ ID NO: 4), or a conservative amino acid substitution thereof.

As used herein, the term "thiolated HA binding peptides" or C-HABPep, means the HABPep disclosed herein which has been chemically modified, using known means in the art, to covalently attach one or more thiol (SH) moieties to the peptide. In some embodiments, this is accomplished by N-terminal addition of a cysteine amino acid.

It will be understood by those of ordinary skill in the art that any known conjugation method which can be used to attach both peptides, HABpep or ECMBpep to the PEG space or any biocompatible spacer through functional reactive groups can be used in the compositions and methods of the present invention.

A biologically compatible polymer refers to a polymer which is functionalized to serve as a composition for creating an implant. The polymer is one that is a naturally occurring polymer or one that is not toxic to the host. The polymer can, e.g., contain at least an imide. The polymer may be a homopolymer where all monomers are the same or a hetereopolymer containing two or more kinds of monomers. The terms "biocompatible polymer," "biocompatible cross-linked polymer matrix" and "biocompatibility" when used in relation to the instant polymers are art-recognized are considered equivalent to one another, including to biologically compatible polymer. For example, biocompatible polymers include polymers that are neither toxic to the host (e.g., an animal or human), nor degrade (if the polymer degrades at a rate that produces monomeric or oligomeric subunits or other byproducts at toxic concentrations in the host).

Polymer is used to refer to molecules composed of repeating monomer units, including homopolymers, block copolymers, heteropolymers, random copolymers, graft copolymers and so on. "Polymers" also include linear polymers as well as branched polymers, with branched polymers including highly branched, dendritic, and star polymers.

An "active agent" and a "biologically active agent" are phrases used interchangeably herein to refer a chemical or biological compound that induces a desired pharmacological or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like.

When the terms "active agent," "pharmacologically active agent" and "drug" are used, it is to be understood that the invention includes the active agent per se, as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

The term "functionalized" as used herein, refers to a modification of an existing molecular segment to generate or introduce a new reactive or more reactive group (e.g., an amine, ester or imide group) that is capable of undergoing reaction with another molecule, polymer or functional group (e.g., an amine, an ester or a carboxyl group) to form a covalent bond. For example, carboxylic acid groups can be functionalized by reaction with a carbodiimide and an imide reagent using known procedures to provide a new reactive functional group in the form of an imide group substituting for the hydrogen in the hydroxyl group of the carboxyl function.

The terms "substituted," "functional group" and "reactive group" are contemplated to include all permissible substituents of organic compounds on the monomers, polymers and networks of interest. In a broad aspect, the permissible substituents include acyclic and cyclic, branched and unbranched, carbocyclic and heterocyclic, aromatic and nonaromatic substituents of organic compounds. Illustrative substituents include, for example, carboxy groups, amine groups, amide groups, hydroxyl groups and so on, as known in the art. The permissible substituents may be one or more and the same or different for appropriate organic compounds.

A functional group or a moiety capable of mediating formation of a polymer or network can be added to a naturally occurring molecule or a synthetic molecule practicing methods known in the art. Functional groups include the various radicals and chemical entities taught herein, and include alkenyl moieties such as acrylates, methacrylates, dimethacrylates, oligoacrylates, oligomethacrylates, ethacrylates, itaconates or acrylamides.

Further functional groups include aldehydes. Other functional groups may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrite and amides of the same acids such as acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene-malonates, isoprene and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid and styrene carboxylic acid. Suitable polyethylenically unsaturated monomers include butadiene, isoprene, allylmethacrylate, diacrylates of alkyl dials such as butanediol diacrylate and hexanediol diacrylate, divinyl benzene and the like.

In some embodiments, other suitable hydrophilic polymers which can serve as the biocompatible polymer include synthetic polymers such as poly(ethylene glycol), poly(ethylene oxide), partially or fully hydrolyzed poly(vinyl alcohol), poly(vinylpyrrolidone), poly(ethyloxazoline), poly (ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers, such as, polysaccharides or carbohydrates such as Ficoll™ polysucrose, dextran, heparan sulfate, chondroitin sulfate or alginate, and polypeptides or proteins such as gelatin, collagen, albumin or ovalbumin, or copolymers or blends thereof.

By way of example, biomaterial compositions of the invention can be used to coat various cartilaginous voids, such as the pleural cavity, or surfaces, for example, such as joints or tendons. Thus, the instant invention relates to a method of tissue augmentation in a host, such as a human patient, wherein said biomaterial of the present invention is introduced at a site of interest using methods known in the art, such as injecting biomaterial at or in a tissue site in need thereof. A kit containing the injectable biomaterials, and a delivery means, such as a syringe, is also provided.

In accordance with an embodiment, the present invention provides a method of treating a cartilage defect in a tissue of a subject comprising administering to the tissue of the subject in need of treatment, a therapeutically effective amount of the biomaterial composition described herein.

In some embodiments, the biomaterial composition described herein can be administered to the site in the subject along with HA in a one-step process. In other embodiments the biomaterial composition described herein can be administered to the site either before or after administering HA to the site.

The term "cartilage defect" as used herein can include any disease or injury induced disruption to the natural cartilage or tissue surface. Examples of such defects include, but are not limited to, damage due to osteo or rheumatoid arthritis, tears, excessive wear of joints due to repetitive use or injury, damage or defects due to other inflammatory or autoimmune diseases.

In certain embodiments, the subject compositions comprise about 1% to about 75% or more by weight of the total composition, alternatively about 2.5%, 5%, 10%, 20%, 30%, 40%, 50%, 60% or 70%, of a biologically active agent.

Various forms of the biologically active agents may be used. These include, without limitation, such forms as uncharged molecules, molecular complexes, salts, ethers, esters, amides, prodrug forms and the like, which are biologically activated when implanted, injected or otherwise placed into a subject.

The specific method used to formulate the novel formulations described herein is not critical to the present invention and can be selected from a physiological buffer (Feigner et al., U.S. Pat. No. 5,589,466 (1996)).

Therapeutic formulations of the product may be prepared for storage as lyophilized formulations or aqueous solutions by mixing the product having the desired degree of purity with optional pharmaceutically acceptable carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

The compositions can take the form of solutions, suspensions, emulsions, powders, sustained-release formulations, depots and the like. Examples of suitable carriers are described in "Remington's Pharmaceutical Sciences," Martin. Such compositions will contain an effective amount of the biopolymer of interest, preferably in purified form, together with a suitable amount of carrier so as to provide the form for proper administration to the patient. As known in the art, the formulation will be constructed to suit the mode of administration.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts, such as Tris, HEPES and other such known buffers can be used.

Preservatives may be added to retard microbial growth, and may be added in amounts ranging from 0.2%-1% (w/v). Suitable preservatives for use with the present invention include phenol, benzyl alcohol, m-cresol, octadecyldimethylbenzyl ammonium chloride, benzyaconium halides (e.g., chloride, bromide and iodide), hexamethonium chloride, alkyl parabens, such as, methyl or propyl paraben, catechol, resorcinol, cyclohexanol and 3-pentanol.

Isotonicifiers are present to ensure physiological isotonicity of liquid compositions of the instant invention and include polhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose or glucose; disaccharides, such as lactose, maltose and sucrose; trisaccharides, such as raffinose; polysaccharides, such as, dextran and so on. Stabilizers can be present in the range from 0.1 to 10,000 w/w per part of biopolymer.

Additional miscellaneous excipients include bulking agents, (e.g., starch), chelating agents (e.g., EDTA), antioxidants (e.g., ascorbic acid, methionine or vitamin E) and cosolvents.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

The present invention provides liquid formulations of a biopolymer having a pH ranging from about 5.0 to about 7.0, or about 5.5 to about 6.5, or about 5.8 to about 6.2, or about 6.0, or about 6.0 to about 7.5, or about 6.5 to about 7.0.

The incubation of the amine-reacting proteoglycan with blood or tissue product can be carried out a specific pH in order to achieve desired properties. E.g., the incubation can be carried out at between a pH of 7.0 and 10.0 (e.g., 7.5, 8.0, 8.5, 9.0, and 9.5). Furthermore, the incubation can be carried out for varying lengths of time in order to achieve the desired properties.

The instant invention encompasses formulations, such as, liquid formulations having stability at temperatures found in a commercial refrigerator and freezer found in the office of a physician or laboratory, such as from about 20° C. to about 5° C., said stability assessed, for example, by microscopic analysis, for storage purposes, such as for about 60 days, for about 120 days, for about 180 days, for about a year, for about 2 years or more. The liquid formulations of the present invention also exhibit stability, as assessed, for example, by particle analysis, at room temperatures, for at least a few hours, such as one hour, two hours or about three hours prior to use.

Examples of diluents include a phosphate buffered saline, buffer for buffering against gastric acid in the bladder, such as citrate buffer (pH 7.4) containing sucrose, bicarbonate buffer (pH 7.4) alone, or bicarbonate buffer (pH 7.4) containing ascorbic acid, lactose, or aspartame. Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10%.

The formulations to be used for in vivo administration must be sterile. That can be accomplished, for example, by filtration through sterile filtration membranes. For example, the formulations of the present invention may be sterilized by filtration.

The biomaterial compositions of the present invention will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the biomaterial to be administered will be governed by such considerations, and can be the minimum amount necessary to prevent, ameliorate or treat a disorder of interest. As used herein, the term "effective amount" is an equivalent phrase refers to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease. For example, a treatment of interest can increase the use of a joint in a host, based on baseline of the injured or diseases joint, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Where necessary, the composition may also include a solubilizing agent and a local anesthetic such as lidocaine or other "caine" anesthetic to ease pain at the site of the injection.

Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

An article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for preventing or treating, for example, a wound or a joint disease and may have a sterile access port (for example, the container may be a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

In accordance with another embodiment, the biomaterials of the present invention provide a method of treating a cartilage defect in a tissue of a subject comprising administering to the tissue of the subject in need of treatment, treatment a therapeutically effective amount of the biomaterial compositions described herein. In other embodiments of the invention, the cartilage defects are in joints or ligaments.

In accordance with an embodiment, the present invention provides the use of the biomaterial compositions disclosed herein, for treating a cartilage defect in a tissue of a subject, characterized in that an effective amount of the biomaterial composition is administered to the tissue of the subject in need of treatment.

In one embodiment, the repair of damaged tissue may be carried out within the context of any standard surgical process allowing access to and repair of the tissue, including open surgery and laparoscopic techniques. Once the damaged tissue is accessed, a composition of the invention is placed in contact with the damaged tissue along with any surgically acceptable patch or implant, if needed.

In accordance with an embodiment, the present invention provides the use of the biomaterial compositions disclosed herein, for treating osteoarthritis in the tissues of a subject, characterized in that an effective amount of the biomaterial composition is administered to the tissue of the subject in need of treatment.

The biomaterials of the present invention can also be used for augmentation of hard tissue within the body of a mammalian subject. Examples of hard tissue augmentation applications include the repair and/or replacement of bone and/or cartilaginous tissue.

In another embodiment the biomaterials of the present invention can also be used for coating the pleural cavity of a subject.

In a further embodiment, the biomaterials of the present invention can also be used for intervertebral disc disease, where lubrication between tissue surfaces is needed and HA binding peptide can increase lubrication at the surfaces.

In accordance with an embodiment, the present invention provides a therapeutic method for the treatment of eye diseases by means of an eye surgery treatment, comprising applying to the eye of a subject in need of such treatment a therapeutically effective amount of the biomaterial compositions described herein. Such surgical procedures include, but are not limited to, corneal transplantation, cataract surgery, glaucoma surgery, and surgery to repair retinal detachment.

In accordance with an embodiment, the present invention provides the use of the biomaterial compositions disclosed herein, for treating eye diseases by means of an eye surgery treatment in a subject, characterized in that an effective amount of the biomaterial composition is administered to the tissue of the subject in need of treatment.

In accordance with another embodiment, the present invention provides a therapeutic method for the treatment of dry eye or keratoconjunctivitis sicca (KCS) which can be the result of a number of disorders, including, for example, Sjogren's syndrome. The inventive methods comprise applying the biomaterial compositions of the present invention on the cornea of the eye, and which may include other therapeutic agents, such as estrogens, or cyclosporine.

In accordance with an embodiment, the present invention provides the use of the biomaterial compositions disclosed herein, for treating dry eye in a subject, characterized in that an effective amount of the biomaterial composition is applied to the eye of a subject in need of such treatment.

It will be understood that the uses provided herein can also include administration of at least one additional therapeutic agent with the compositions disclosed herein.

It will also be understood that the uses provided herein can also include when the biomaterial is administered together with HA in one step.

In accordance with an embodiment, the present invention provides a method for making the biomaterial composition as described herein, comprising: a) obtaining a sufficient amount of one or more biocompatible polymers conjugated to at least one or more N-succinimide groups and one or more maleimide groups in a suitable solution; b) adding to the solution of a) a sufficient amount of one or more ECMBPep and allowing it to react with the one or more N-succinimide groups to produce one or more biocompatible polymers having one or more ECMBPep which are covalently linked to the biocompatible polymers; c) obtaining a sufficient amount of having one or more thiolated HA binding peptides (C-HABPep) in a suitable solution; d) adding the solution of b) to the solution of c) and mixing for a sufficient period of time to produce one or more biocompatible polymers having one or more HA binding peptides (HABPep) which are covalently linked to the biocompatible polymers which are covalently linked to one or more ECMBPep; e) adding to the solution of d) a sufficient amount of hyaluronic acid (HA) in a suitable solvent for a sufficient time to allow HA to bind to the HABPep in the solution; f) removing the unreacted reagents of b), c) and e) and purifying the remaining product.

It will be understood by those of ordinary skill in the art that any biocompatible polymer can be used in the inventive methods. In a preferred embodiment, the biocompatible polymer is poly(ethylene glycol).

In accordance with an embodiment, the present invention provides a bifunctional biopolymer composition comprising a biologically compatible polymer having at least one amine reactive moiety and at least one thiol reactive moiety.

The term "bifunctional biopolymer composition" means a biocompatible polymer which has been chemically modified to have at least one amine reactive moiety and at least one thiol reactive moiety covalently linked to the polymer either directly or via a linking moiety.

In one or more embodiments, the amine reactive moiety can include N-hydroxysuccinimide or N-hydroxysulfosuccinimide. Other bifunctional biopolymer compositions can include, for example, maleimide-PEG-N-hydroxysuccinimide; iodoacetamide-PEG-hydroxysuccinimide/sulfsuccinimide; and acrylate-PEG-N-hydroxysuccinimide. Other molecules such as azlactones, imidoesters, epoxides, fluorophenyl ester, anhydride, caronate, acyl azide, isothiocyanate, isocyanate, aldehyde, etc. can also be used.

In one or more embodiments, the thiol reactive moiety can include maleimide or iodoacetamide.

One of ordinary skill in the art will understand that the chemical modifications to the biopolymers to incorporate the amine reactive moieties and thiol reactive moieties are known in the art and can be accomplished using known methods.

In accordance with an embodiment, the present invention provides a method for coating a tissue surface with a biomaterial composition described herein having one or more HA binding peptides and one or more ECM binding peptides comprising administering to the tissue of the subject an effective amount of the biomaterial composition.

In accordance with an embodiment, the present invention provides a method of treating a cartilage defect in a tissue of a subject comprising: a) administering to the tissue of the subject in need of treatment, an effective amount of the biomaterial composition to create a cartilage defect coated with a biologically compatible polymer having one or more HA binding peptides.

In one or more embodiments, the at least one amine reactive moiety of the bifunctional biopolymer composition described herein is N-hydroxysuccinimide.

In one or more embodiments, the at least one thiol reactive moiety of the bifunctional biopolymer composition described herein is maleimide.

In one or more embodiments, the biologically compatible polymer of the bifunctional biopolymer composition described herein is PEG.

It will be understood that the bifunctional biopolymer compositions can include other suitable amine and thiol reactive moieties known in the art. Examples would include N-hydroxysulfosuccinimide and iodoacetamide.

EXAMPLES

Synthesis of hyaluronic acid binding peptide. Thiolated hyaluronic acid binding peptide (C-HABPep; sequence CRRDDGAHWQFNALTVR (SEQ ID NO: 2)) was synthesized using standard Fmoc-mediated solid phase peptide synthesis on a Symphony Quartet peptide synthesizer (Protein Technologies). Following synthesis, peptides were cleaved using a solution of trifluoroacetic acid, triisopropylsilane, and water in a 95:2.5:2.5 ratio. Crude product was purified using reverse-phase high performance liquid chromatography (HPLC, C18 Grace-Vydac column) on a water/acetonitrile gradient. Purified peptides were frozen and lyophilized; identity of purified peptides was confirmed using matrix assisted laser-desorption ionization time of flight (MALDI-TOF) mass spectroscopy (Voyager DE-STR, Applied Biosystems).

Preparation of HA-binding coatings by covalent strategy. C-HABPep was conjugated to articular cartilage through a heterobifunctional poly(ethylene glycol) (PEG) spacer. Maleimide-PEG-N-hydroxysuccinimide (MAL-PEG-NHS, 3.5 kDa, Jenkem Technologies), which has functionalities that are thiol- and amine-reactive, was dissolved to 5 mM in 50 mM sodium bicarbonate, pH 7.5 and added to the articular surface. The NHS groups were allowed to react with endogenous amines on the cartilage surface for 30 minutes. PEGylation was confirmed by attenuated total reflectance Fourier transform IR spectroscopy (ATR-FTIR; Bruker Vector 22 with a Pike Miracle ATR attachment). Following thorough washes in buffer to remove unreacted crosslinker, a 1.5 mM solution of C-HABPep was added to the surface to react with maleimide groups for an additional 30 minutes. Surfaces were carefully washed to remove unreacted peptide, yielding a cartilage surface with covalently attached HA-binding functionality.

Preparation of HA-binding coatings by non-covalent strategy. ECMBPep were conjugated to a heterobifunctional poly(ethylene glycol) (PEG) spacer. Maleimide-PEG-N-hydroxysuccinimide (MAL-PEG-NHS, 3.4 kDa, Jenkem Technologies), which has functionalities that are thiol- and amine-reactive, was reacted with the amine end group of the peptides (collagen I binding peptide: YSFYSDESLQ (SEQ ID NO: 3), collagen II binding peptide: WYRGRL (SEQ ID NO: 4)) in sodium bicarbonate solution (pH 8.3), followed by conjugation of thiol end group of the HABpeptide to the MAL end group of the PEG space. This polymer-peptide solution (1.25 mg/mL) was mixed with either HA (Lifecore, 975 KDa) or HA-rhodmaine (Creative PEGworks, 970 kDa), HA-fluorescein (Creative PEGworks, 970 kDa). After solution was properly dissolved 500 µL was added to each well of the 24 well plate that the cartilage explants were in. The quantity of solution covered the disks, the plates were then placed on a shaker at low rpm overnight. After the incubation, samples were washed thoroughly for 4-6 hours in PBS at high rpm before mechanical testing.

In another embodiment for one-step application, thiol-PEG-succinimidyl glutaramide (SGA) (3.5 kDa,) was reacted with HABpep (GAHWQFNALTVR) (SEQ ID NO: 10) (dissolved in dimethyl sulfoxide) in a PBS buffer (pH 7.4) for 4 hours. After dialysis and lyophilization, thiol functionality of the product was reacted overnight with vinyl functional groups of vinyl dimethyl azlactone using a Michael addition reaction in the presence of dimethylphenylphosphine in dimethyl sulfoxide at room temperature. The product was dissolved in water and washed multiple times with cold ether and dried in vacuo. The resultant product was added to a sodium bicarbonate solution (pH 8.3) of collagen binding peptide (Col II-WRYGRLC (SEQ ID NO: 4), Col I-YSFYSESLQ (SEQ ID NO: 3)). After 4 hours of reaction time, the solution was dialyzed against water (MWCO 2000 Da) and lyophilized to yield a white fluffy powder.

X-ray photoelectron spectroscopy. XPS was performed to verify the presence of the HA-binding coating on articular cartilage. Lyophilized cartilage samples were adhered to the specimen stage and loaded into a PHI 5400 XPS instrument at ultra-high vacuum. The samples were analyzed using Mg $K\alpha$ X-rays (1253.6 eV), and spectra were acquired at a take-off angle of 45°. Atomic concentrations were determined by integration of the relevant photoelectron peaks using commercially available software (CasaXPS).

Visualization of the HA-bound layer. Cartilage was conjugated with C-HABPep and incubated with biotinylated HA synthesized as previously described. Briefly, HA (975 kDa) was dissolved in 50 mM boric acid, pH 5.2 at 2 mg/ml. This was combined with biotin hydrazide (Sigma) in a 20:1 weight ratio. N-(3-Dimethylaminopropyl)-N'-ethylcarbodiimide hydrochloride (EDC, Sigma) was added to a final concentration of 100 mM. The reaction was allowed to proceed at room temperature for 16 hours, after which it was dialyzed to remove unreacted biotin hydrazide and EDC. HA-biotin was lyophilized and stored at −20° C. for later use. Following incubation with 5 mg/ml HA-biotin, HAB-Pep-functionalized cartilage samples were washed vigorously to remove unbound HA-biotin. Presence of biotin was visualized using streptavidin and horseradish peroxidase based on the Histostain SP kit (Invitrogen).

Cartilage sample preparation for lubrication testing. Cartilage samples were prepared for lubrication testing as a modification on previously published protocols (Arthritis and rheumatism 56, 882-891, (2007); Arthritis and rheumatism 50, 516-525, (2004)). Both normal and osteoarthritis tissue samples were ordered through (NDRI, Philadelphia, Pa.). Tissue samples were received within 24 hours postmortem or surgery. Normal and diseased samples were received in a sterile container containing Dulbecco's Modified Eagle Medium (DMEM), and protease inhibitor cocktail. Biopsy punches were used to isolate cylindrical disks (radius=6 mm) and annuli (outer radius=4 mm, inner radius=1.5 mm) with small holes punctured through the cylinder walls to improve fluid depressurization. Due to the 24-hour time point in media washing for 24-hours to eliminate any lubricin, HA, and SAPLs; instead samples were washed for 4-6 hours in PBS on a shaker. HA sample groups were always incubated in HA solution (5 mg/mL) for 24-hours post-washing (FIGS. 4b,c). It should be noted that human cartilage was scarce especially in OA samples received.

Figure 3:
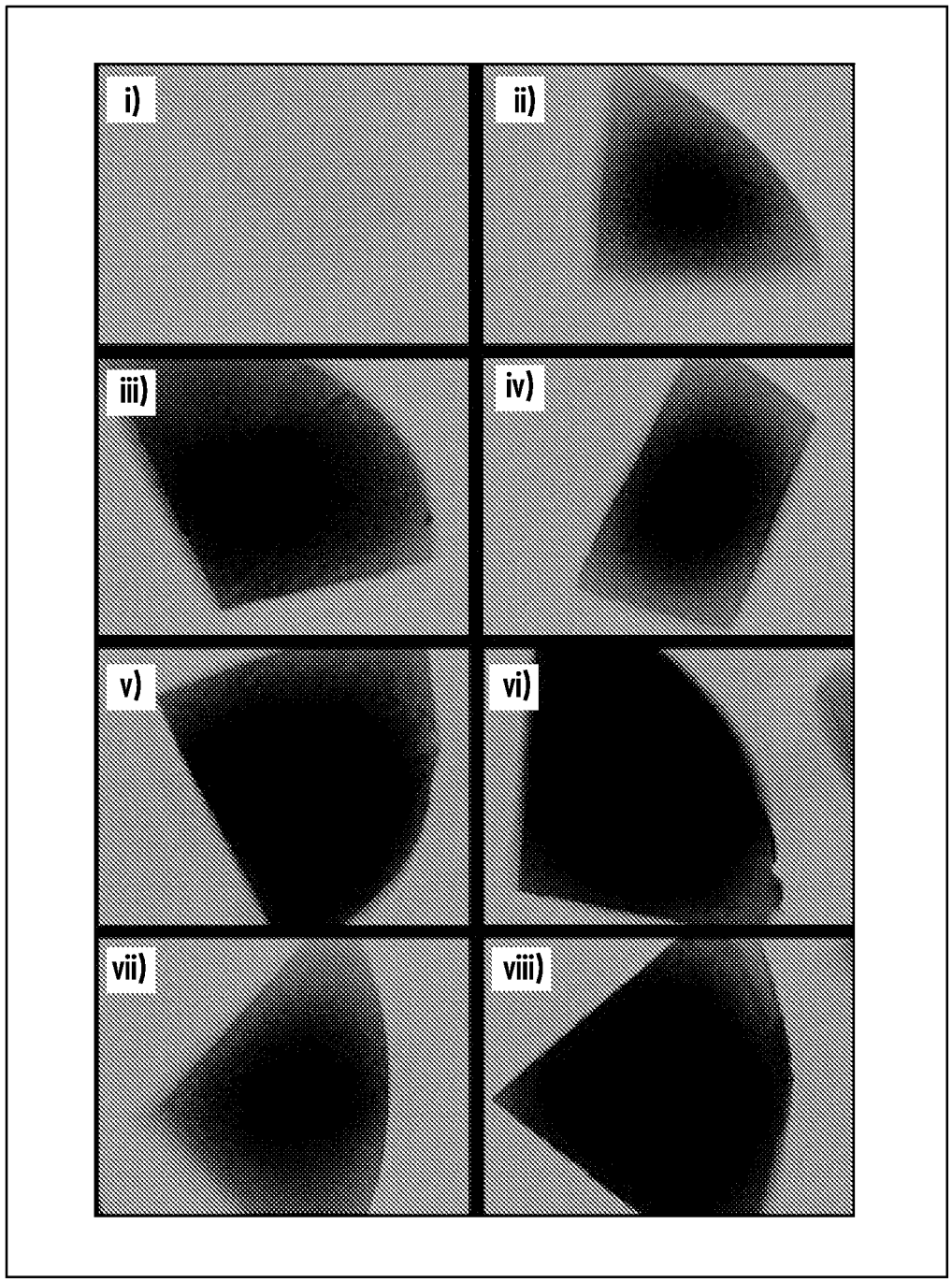
FIG. 3 depicts the biomaterial-HA coating of the present invention on a cartilage tissue surface. HA coating on the cartilage tissue surface was evaluated by fluorescence imaging that showed compared to the controls (both, only PEG and HA-rhodamine) and scrambled peptide, collagen II binding peptide based biomaterial-HA system remain inbound to the cartilage surface with more intensity. i) PEG only, ii) HA-rhodmaine only, iii) scrambled collagen I binding peptide (YFDEYSLSQS (SEQ ID NO: 5)), iv) collagen I binding peptide (YSFYSDESLQ (SEQ ID NO: 3)), v) scrambled collagen II binding peptide (YRLGRW (SEQ ID NO: 6)), vi) collagen II binding peptide (WYRGRL (SEQ ID NO: 4)), vii) scrambled sequence of fibronectin binding domain of collagen II (QFYDTRTSE (SEQ ID NO: 7)), viii) fibronectin binding domain of collagen II (QDSETRTFY (SEQ ID NO: 8)).

In later experiments, covalent modification of cartilage surface by HABpep (FIG. 1) was performed on bovine articular cartilage samples. All non-covalent HABpep modification and in vitro lubrication studies were performed using human articular cartilage samples (FIG. 3). Normal human tissue was isolated from cadavers with ages 51 (F) and 78 (M) years. Human OA cartilage samples were isolated from the patients with ages, 58 (F), 60 (F), 61 (M), 65 (M), 69 (M), 71 (F), who underwent total knee arthroplasty. Care was taken to avoid damaging the articular surface during dissection. Samples (outer diameter=8.0 mm, inner diameter=3.0 mm) were microtomed and evenly cut to obtain a flat surface. The superficial layer was maintained intact and only the deep layer of cartilage was cut to obtain a flat layer to glue to the metal counter-surface while friction measurements. Cartilage was used fresh without freezing or the addition of protease inhibitors so as not to change the surface lubrication properties. Samples were washed vigorously in PBS overnight to deplete the cartilage surface of any residual synovial fluid, after which they were functionalized with an HA-binding layer as needed and incubated at 4° C. for about 24 hours in the test lubricant. HABpep modified cartilage samples were soaked overnight in HA bath (5.0 mg/mL, 975 kDa) followed by washing them vigorously in PBS overnight to remove unbound HA. These samples were incubated in PBS for 1 hour and lubrication testing was performed. Cartilage samples with no HABpep modification were incubated in either PBS or HA (5.0 mg/mL, 975 kDa) for 1 hour, after 24 hours PBS wash, and lubrication testing was performed.

Histology and India ink staining of cartilage samples. After mechanical testing of human normal and diseased samples was completed, samples were imaged with Zeiss Discovery V2 dissection imaging microscope. India Ink (Becton Dickson, Cockeysville, Md.) was applied to the surface for characterization of the severity of damage. Part of the sample was then embedded in paraffin wax for Safranin-O histological staining. Some human samples were embedded via liquid nitrogen freezing and put on slides with Tissue Embedding Media (Thermo Scientific, Logan, Utah)

and sectioned with a cryomill (Leica). Histological staining of samples was done in accordance to the Elisseeff staining protocol for Safranin-O. After samples were dehydrated and cut in half-circles in order to see topography the safranin-o staining procedure was implemented. Materials were as follows: Safranin-O (ScholAR Chemistry 9466802) (stains proteogylcans (GAGs) red), Fast Green, FCF (Sigma F-7258) (counterstains tissue green), Glacial Acetic Acid (Sigma A6283). Concentrations of each were: 0.1% Fast Green (FCF) solution (500 mg Fast Green/500 mL of $dH_2O$), 1% Glacial Acetic Acid solution (1 mL/99 mL $dH_2O$), and 0.1% Safranin-O solution (100 mg Safranin-O/ 100 mL $dH_2O$) (pH 3.1 using concentrated HCL). The paraffin embedded cartilage samples were cut in a thickness of 5 μm and placed in a 400° C. water bath for a few seconds, then put on glass slides. Slides were then left on 400° C. hot plate overnight. Next, rehydration was implemented first Xylene twice for 1 minute, then 100% EtOH twice 1 minute each, third 95% EtOH twice for 1 minute each, fourth 80% EtOH once for 1 minute, finally $dH_2O$ twice for 5 minutes each. Slides were dried and moved to a dry holder. Staining occurred next by placing slides in Fast Green for 3 minutes, then acetic acid for 10 seconds, after they were dried and moved to another dry holder and placed in the Safranin-O solution for 10 minutes for the final step of staining Washing was then necessary in this order: $dH_2O$ three baths for 1 minute each, second 95% EtOH 1 minute, 100% EtOH 1 minute, finally Xylene for 1 minute. Samples were then mounted with a cover slip using Permount Mounting Solution and left 24 hours to dry.

Lubrication testing. Boundary lubrication testing of articular cartilage-cartilage contacts was performed by modifying a previously published protocol (*Osteoarthritis Cartilage* 15, 35-47, (2007)). Briefly, a cartilage disk and annulus were adhered with cyanoacrylate glue to parallel plate fixtures of a RFS-3 rheometer (Rheometric Scientific). The samples were bathed in the test lubricant, measured with digital calipers, compressed to 82% of their original combined height, and preconditioned by rotating 2 revolutions in each direction at an effective sliding velocity of 3 mm/s, which is defined as the angular velocity times the effective radius of the annulus $Reff=\frac{2}{3}[(Ro3-Ri3)/(Ro2-Ri2)]=2.94$ mm. This preconditioning was repeated twice more, followed by a two hour stress-relaxation period to allow the pressurization of the fluid in the compressed cartilage to fully subside, leaving only boundary effects for the lubrication testing.

Lubrication testing was then performed by 2 rotations in each direction at an effective sliding velocity of 0.3 mm/s Samples were allowed to relax between tests for 1200, 120, 12, and 1.2 seconds. Lubrication testing was then carried out by reversing the order of the revolutions (turning first clockwise instead of counter-clockwise) with the same pre-test relaxation periods as before. During each test, torque (τ) and normal force (N) were measured, and instantaneous measurements of μk, the kinetic friction coefficient, where determined from the following equation: $\mu k=\tau/(Reff*N)$. Instantaneous μk values were averaged over the second revolution in each direction to produce an average <μk> that was used for comparisons. Generally, differences between coefficients for forward and backward revolutions were very small, so <μk> data shown is only from a single direction of rotation. Static friction coefficients were calculated as the instantaneous $\mu s=\tau max/(Reff*N)$ at the maximal torque value found during the startup period of the test.

Friction measurements on the human cartilage samples treated to remove lubricin. Lubricin was removed from the human cartilage samples in accordance to a published procedure by Jones, A. R. et al. *J. Orthop Res.* 25, 283-292 (2007).

In brief, endogenous lubricin was extracted from cartilage discs on incubation at room temperature for 20 minutes in PBS containing 1.5 M NaCl followed by an additional 20 min incubation in pH 6.2 of 4M Guanidine-HCl solution. The cartilage discs in each solution were shaken throughout the experiment. Friction measurements on these samples were performed by procedures as described herein.

In vivo imaging for HA retention. In vivo imaging was conducted on 6 to 8 weeks-old male Sprague Dawley Rats (n=4 for each group; total=8). The rats were anesthetized with isofluorane under a pre-established protocol (The Johns Hopkins University Animal Care and Use Committee approved the animal procedures, protocol#RA12A136). Each rat was injected with 50 μL solution mixture of HA-rhodamine (20 mg/mL, CreativePEGworks) with HABpep polymer (10 mg/mL) under sterile conditions penetrating the joint capsule and bursa. After injection, rats were imaged and kept under isofluorane anesthesia with an IVIS Spectrum In-Vivo Imaging System (Rats were imaged at different time points: immediately after surgery (<2 hours), 6 hours, 24 hours and 72 hours after surgery). All images were taken at the same excitation (570 nm) and emission (620 nm). Rats were anesthetized before each imaging time point. A method for semi-quantitative analysis of HA bound on the cartilage surface is described in supplementary information.

Ocular surfaces and contact lens modification. Rabbit eyes (8 weeks to 12 weeks old rabbits purchased from Pel-Freez Inc, AK) were processed ex vivo to separate epithelial layers from the sclera, conjunctiva and cornea. Each of these tissues was cut into small pieces using a 3-mm diameter biopsy punch, and washed rigorously with PBS. To these tissues, a solution of HA-fluorescein (975 kDa, CreativePEGworks), mixed with HABpep-PEG-Col IBpep polymer was added (final concentration 5.0 and 1.0 mg/mL, respectively), kept on a shaker for 2 hours and washed with PBS before taking images by Zeiss Discovery V2 imaging microscope. The ability of the HABPep technology to bind HA to multiple different external ocular tissues was tested and compared to controls for each tissue using fluorescein labeled HA. Tissue samples were cut from biopsy punches and separated into three equal pieces and treated with HA alone (negative control for nonspecific HA binding), HA with scramble peptide (control for nonspecific peptide binding) and HA with col IBpep). All ocular tissues were imaged at the same exposure time and magnification. Contact lens (PuriVision from Bausch & Lomb was treated with diazirine-based photo-leucine (5.0 mg/mL) under UV light (365 nm) for 30 minutes at an approximate distance of 3.0 cm, followed by reacting the amine groups with azlactone functionality of the PEG-HABpep (1.0 mg/mL) in a sodium bicarbonate solution (pH 8.3) for 4 hours. HABpep-modified contact lenses were added to a solution of HA-rhodamine (1.0 mg/mL) and kept on a shaker for 2 hours. After washing with PBS, fluorescence images were taken by Zeiss Discovery V2 imaging microscope and processed with ImageJ. To measure water evaporation rate from the contact lens, an evaporation cell was designed by cutting the cap and hinge off a 1.5-mL SealRite® microcentrifuge tube (USA Scientific, Inc.). After filling the cell with 1.2 mL of Hank's buffer solution (HBSS), the contact lens was glued with instant Krazy Glue® (Elmer's Products) to the rim of the cell. The cell was gently placed on its side, keeping the contact lens inside completely hydrated, into an analytical balance and the weight of the cell was recorded at the start and every 5 minutes for 50 minutes (n=3).

Data and data analysis. All experiments were performed in triplicate. Quantitative biochemical data was evaluated using multifactor analysis of variance (ANOVA) to determine the significance of main factor effects to a significance level of 0.05. Multiple comparisons of individual condition means was carried out using Tukey's honestly significant difference (HSD) test. Statistical analysis was carried out in MATLAB (Mathworks).

Example 1

The biomaterial compositions were first applied to cartilage tissue (FIG. 1a). An HA-binding peptide was covalently bound to the cartilage surface via a heterobifunctional poly(ethylene glycol) (PEG) chain (FIG. 1b). The HA-binding peptide-polymer therapy was designed to noncovalently bind HA (endogenously produced or exogenously injected) to the tissue surface (FIG. 1b). It was thought that by localizing HA to the surface of articular cartilage, it would enhance the boundary lubrication effects of free HA in the synovial fluid and mimic the presumed role of lubricin to improve joint lubrication in a healthy knee. In addition, HA has a number of biological functions that would be ideal to concentrate at the tissue surface including reducing inflammation, mediating matrix metalloproteinase expression and protecting cells from radical damage. Coating the surface with HA can also physically protect the cartilage surface from cytokines and degrading enzymes that are frequently found in a diseased or post-truamatic joint. Finally, and most critically, the presence of the polymer-HA binding modification provides a self-healing mechanism to concentrate HA on a tissue surface. Numerous endogenous enzymes can degrade HA and its fluid concentrations can quickly decrease with normal turn over. The HA-binding peptide can recapture HA that is lost through a physical or biological mechanism and provide the stable anchor on the tissue surface that is necessary to dynamically bind and concentrate HA where it is needed.

Articular cartilage tissue explants were functionalized with PEG spacers and HA-binding peptide (HABpep) by both covalent and non-covalent methods. The PEG spacer was functionalized with an amine-reactive N-hydroxysuccinimide (NHS) group as well as a thiol-reactive maleimide (MAL) group to generate the heterobifunctional NHS-PEG-MAL. First, the NHS-PEG-MAL was covalently reacted with the amine-rich cartilage surface to produce a thiol-reactive surface that could be readily exposed to a thiolated HABpep. PEGylation of articular cartilage was confirmed by attenuated total reflectance Fourier transform infrared (ATR-FTIR) spectroscopy that compared coated cartilage surfaces to unmodified control cartilage explants. Polymer-modified surfaces produced spectra that indicated a large peak at ~1066 cm-1, consistent with the ether bonds of the PEG spacer, that was not present on unmodified cartilage, (FIG. 1c). Additionally, X-ray photoelectron spectroscopy (XPS) spectra of the PEGylated cartilage compared to native cartilage demonstrated a significant decrease in nitrogen content and a drop in the carbon to oxygen ratio (closer to 2, the ratio in PEG), indicating that a synthetic, lower-nitrogen containing layer had been successfully grafted to the cartilage surface (FIG. 1d). Thiolated HABPep (C-HAB-Pep) was then readily grafted to the PEG-MAL coating. HA binding peptide functionalization of the polymer coating was confirmed by incubation of the cartilage with HA labeled using biotin hydrazide and 1-ethyl-3-(3-dimethyl-aminopropyl) carbodiimide (data not shown). Following extensive washing, cartilage surfaces were incubated with streptavidin-conjugated horseradish peroxidase and stained to confirm the presence of HA-biotin. A greater intensity of staining was observed on material modified surfaces compared to control cartilage incubated with HA-biotin alone (FIG. 1e).

Example 2

Figure 2:
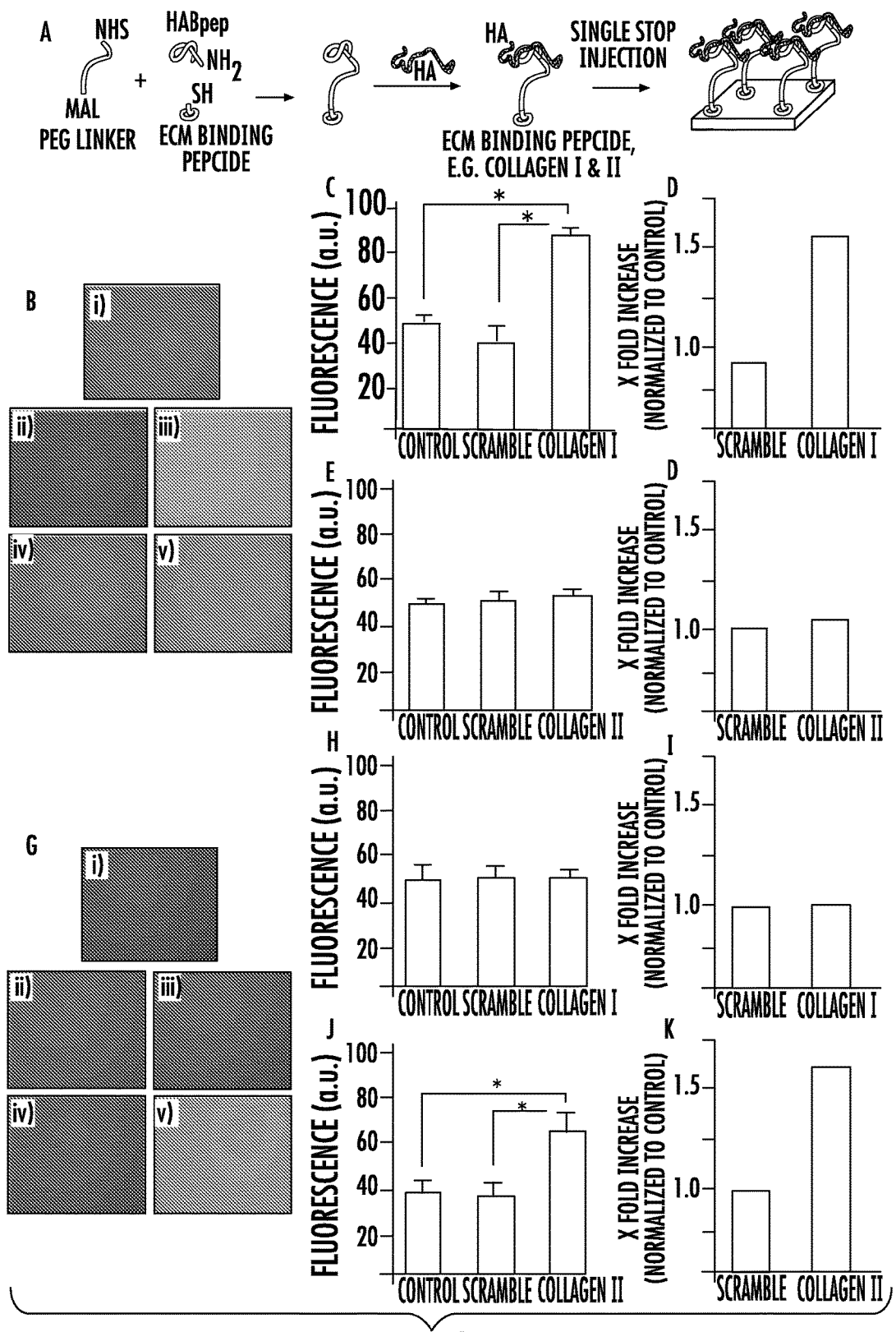
FIG. 2 depicts the clinically-relevant, non-covalent strategy, for one-step application of HA binding polymer system on tissue surface of the present invention. 2A, The first step in this strategy for coating a tissue surface is the reaction of a maleimide-PEG-NHS crosslinker with primary amines of the HA-binding peptide. Subsequently, peptides that non-covalently bind to ECM components, such as collagen I and collagen II, also having a thiol end group, is reacted to the maleimide. Finally, this polymer-peptide system of the present invention is mixed with an HA solution that binds to the peptide-polymer system, which on a single application makes a biomaterial-HA coating on the tissue surface. The binding of the collagen binding peptides were analyzed on thin coatings of collagen I and II on polystyrene tissue culture plates. A thin coating of collagen I on TCP with: 2B, i) No peptide, only PEG-fluorescein as a control, ii) scrambled collagen I binding peptide conjugated to PEG-fluorescein, iii) collagen I binding peptide conjugated to PEG-fluorescein, iv) scrambled collagen II binding peptide conjugated to PEG-fluorescein, v) collagen II binding peptide conjugated to PEG-fluorescein. 2C, Fluorescence intensity showed significant binding of collagen I binding peptide on collagen I coating compared to control and scrambled peptide. 2D, Normalized fluorescence intensity showed collagen I binding peptide remain inbound to collagen I coating, 1.55 times to that of scrambled peptide (even after washing). 2E, Fluorescence intensity showed no significant binding of collagen I binding peptide on collagen II coating compared to control and scrambled peptide. 2F, Normalized fluorescence intensity showed collagen I binding peptide did not bind to collagen II coating and was comparable to the scrambled peptide. A thin coating of collagen II on TCP with: 2G, i) No peptide, only PEG-fluorescein as a control, ii) scrambled collagen I binding peptide conjugated to PEG-fluorescein, iii) collagen I binding peptide conjugated to PEG-fluorescein, iv) scrambled collagen II binding peptide conjugated to PEG-fluorescein, v) collagen II binding peptide conjugated to PEG-fluorescein. 2H, Fluorescence intensity showed significant binding of collagen II binding peptide on collagen II coating compared to control and scrambled peptide. 2I, Normalized fluorescence intensity showed collagen II binding peptide remain inbound to collagen II coating, 1.65 times to that of scrambled peptide (even after washing). 2J, Fluorescence intensity showed no significant binding of collagen II binding peptide on collagen I coating compared to control and scrambled peptide. 2K, Normalized fluorescence intensity showed collagen II binding peptide did not bind to collagen I coating and was comparable to the scrambled peptide.

Second, a clinically relevant one-step injection/coating technology of the present invention was developed based on non-covalent binding of the HABpeptide-polymer system. Tissue surfaces, including, for example, articular cartilage, conjunctiva and sclera of an eye, are collagen I and II enriched, and can act as stable anchoring sites for the ECM binding peptides (ECMBPep). The HA-binding peptide that is linked to the ECMBPep through the PEG spacer can recapture HA that is lost through a physical or biological mechanism and can dynamically bind and concentrate HA where it is needed. Specifically, amine functionality of Col I and II ECMBPep were reacted with NHS-PEG-MAL followed by conjugation of C-HABPep to the Maleimide end groups. The resultant biomaterial composition of the present invention is mixed with HA and applied to tissue surfaces in a single step (FIG. 2A). Fluorescence staining of ECMBPep on tissue culture plates coated with collagen I and collagen II (FIGS. 2B-K) and articular cartilage explants (FIG. 3) showed specific binding of ECMBPep to the surfaces.

Example 3

Since HA injected into a joint is quickly cleared and HA is in low concentration in a diseased environment, a key test of the polymer-modified hyaluronic acid-binding surface is the ability to retain the benefit of increased lubrication after HA is no longer present in the environment. HA-binding coatings without exogenous lubricant were able to replicate the low friction characteristics of native cartilage tested with physiological levels of HA lubricant. Cartilage surfaces treated with the HA-binding polymer system were incubated with HA solutions. After incubation, the tissue samples were thoroughly washed to remove any unbound HA and lubrication was tested in PBS without any HA.

Figure 4:
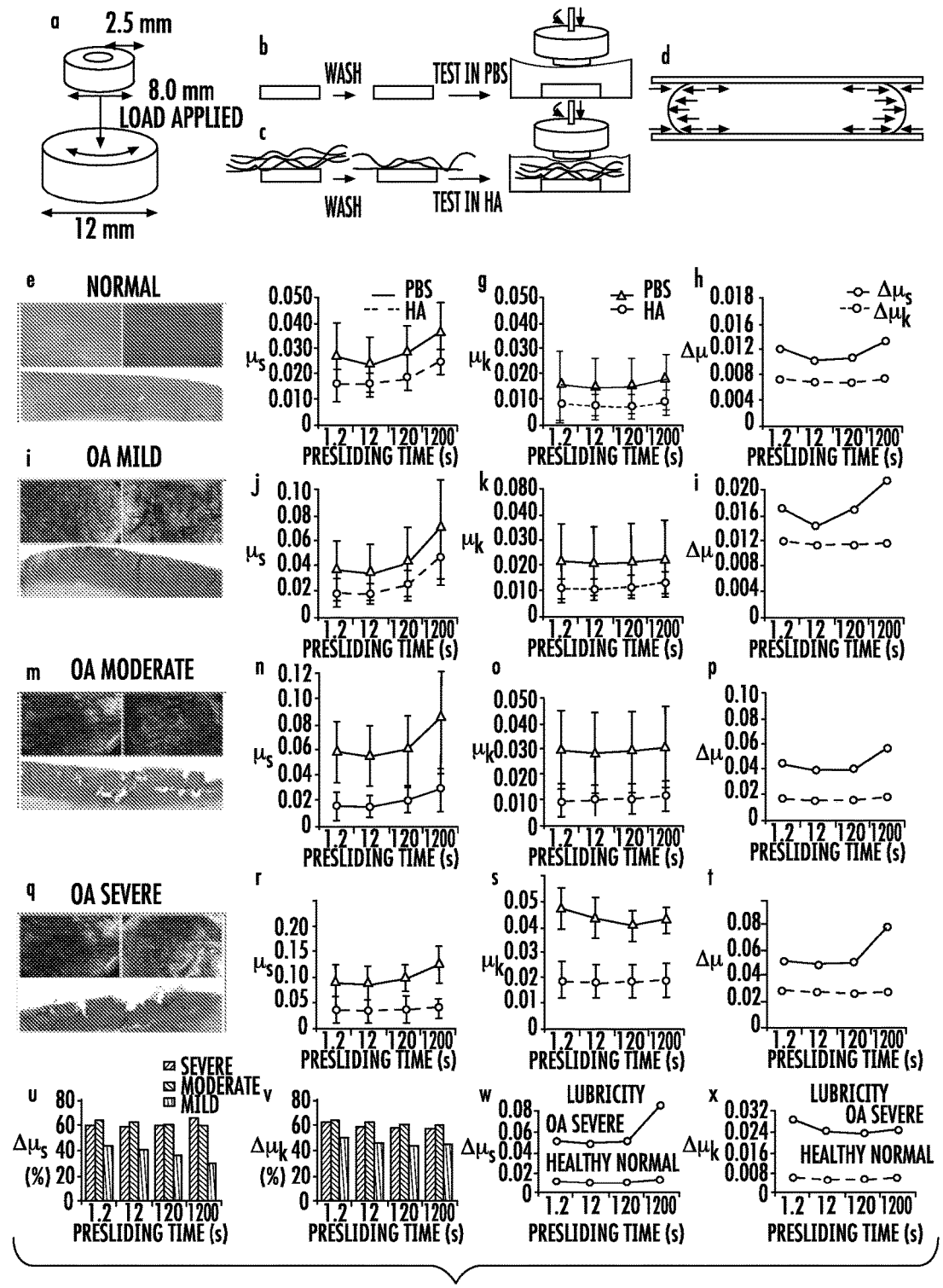
FIG. 4 depicts lubrication testing of articular cartilage without binding peptide. Friction measurements and lubrication analysis for articular cartilage surfaces. 4a, Lubrication of articular cartilage was evaluated using a cartilage disk and annulus rotated in opposite direction. Cartilage samples were isolated and incubated in either control PBS (4b), or an HA lubricant solution (4c). Samples were compressed 18% and rotated 720° in each direction. 4d, Forces occurring during lubrication testing between the two articular cartilage surfaces. Red arrows indicate opposite force applied from the coated surface. Cartilage tissue samples were divided into different subgroups from normal to severely damaged samples for lubrication analysis. Representative histology images and gross topography, graphs of static friction, kinetic friction and lubricity vs. pre-sliding time (s) for each of the subgroups in the respective order: 4e, f, g & h for normal healthy cartilage samples; 4i, j, k & l for mild OA samples; 4m, n, o & p for moderate OA samples; 4q, r, s & t for severe OA samples. 4u, Static friction percent reductions of all OA stages in PBS vs. HA solution. 4v, Kinetic friction percent reductions of all OA stages in PBS vs. HA solution. Comparison of static, 4w, and kinetic, 4x, lubricity values ($<\mu>PBS-<\mu>HA$) of a severely damaged OA sample with a healthy cartilage sample.

Diseased tissue represents a further challenge, as it is characterized by a rough, fibrillated surface with very different frictional properties. Multiple pathogenic mechanisms can lead to cartilage deterioration and not necessarily correlate to higher friction values, including inflammatory and other biochemical pathways. The results from our mechanical testing however suggested that in vitro degenerated cartilage exhibited higher friction values compared to normal samples using the cartilage-on-cartilage mechanical testing protocols (FIG. 4). A number of recent studies also found a similar correlation of increasing osteoarthritis stage and increasing frictional response; however, the increased potential for OA cartilage pressurization may be considered a factor. Tribological studies of diseased human cartilage (OA) explants, categorized by severity of cartilage damage, suggested that HA improved the lubrication properties of the diseased tissue to an even greater degree than normal tissue. An increasing HA lubrication effect was observed proportional to the severity of OA cartilage (FIGS. 4u,v). The static and kinetic lubricity values ($<\mu>$ in PBS-$<\mu>$ in HA) for the most severely damaged OA samples were approximately 5 times higher (FIGS. 4w,x) than those of the normal "healthy"

cartilage samples. These values directly relate to the surface damage and low lubrication values in OA cartilage samples and highlight the need and increased benefit for enhanced lubrication and delivery of HA to the diseased environment.

Example 4

Figure 5:
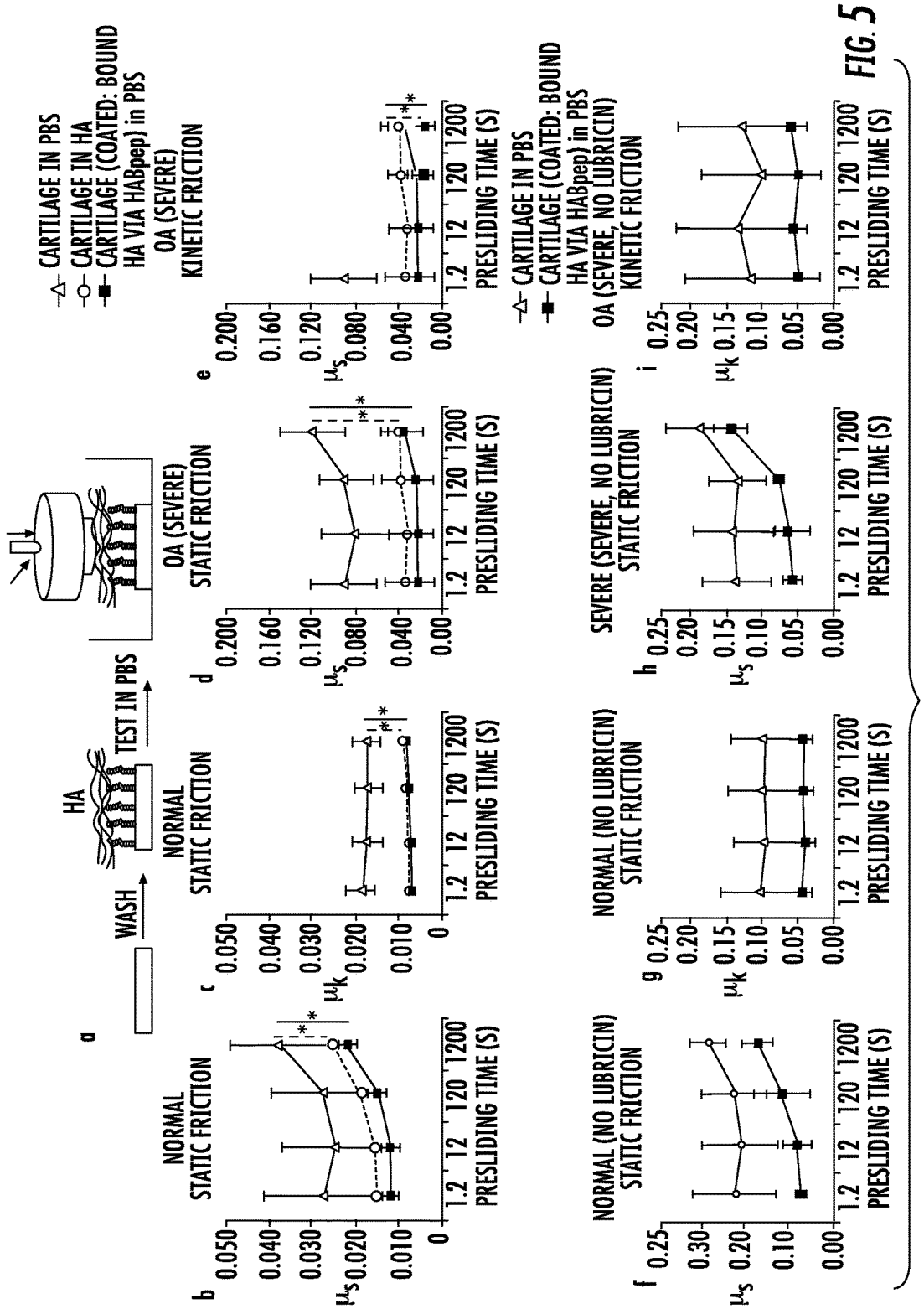
FIG. 5 depicts the cartilage surface-bound HA via the HABpep-polymer coating system in the absence of an exogenous lubricant can recapitulate the friction coefficients of high concentration HA lubricants. 5a, Representative schematic of an embodiment of the present invention for the preparation and incubation of HABpep coated samples in test solution PBS. Lubrication properties of normal cartilage and severely damaged cartilage coated with the polymer-peptide system were tested in the presence of saline, and compared with uncoated surfaces in either saline or HA. Representative graphs of static friction and kinetic friction vs. pre-sliding time (s) for the normal cartilage sample (5b & c) and severely damaged cartilage sample, OA stage 3-4 (5d & e). (For statistical analyses: dashed lines represent cartilage samples (no HABpep modification) in PBS vs. HA bath and solid lines represent cartilage samples in PBS vs. cartilage samples coated with bound HA via HABpep in PBS.) Cartilage surface-bound HA via the HABpep-polymer coating system reduced friction values when lubricin is extracted from the tissue. Lubrication properties of normal cartilage and severely damaged cartilage (lubricin removed) coated with the polymer-peptide system was measured in PBS and compared to controls. Representative graphs of static friction and kinetic friction vs. pre-sliding time (s) for the normal cartilage sample (5f & g) and severely damaged cartilage sample, OA stage 3-4 (5h & i).

Since the physical lubrication properties of HA are a key therapeutic modality of function in the joint, we further investigated the impact of surface modification. In particular, we compared this to the lubricity of cartilage treated with the surface modification (surface-bound HA only) versus untreated cartilage in a bath of HA. The static and kinetic total friction values for normal cartilage tissue decreased significantly (35% and 72%, respectively, FIGS. 5b,c) when tested in an HA bath ($<\mu s>$ of 0.018 and $<\mu k>$ of 0.008) compared to a PBS bath ($<\mu s>$ of 0.028 and $<\mu k>$ of 0.028). Cartilage samples were then coated with HABpep-PEG-Col IIBpep polymer, pretreated with HA, thoroughly washed to remove unbound HA, and mechanically tested in phosphate buffered saline (PBS) (FIG. 5a & experimental setup pictured in FIG. 4c). With application of the HABpep coating and HA pretreatment, the cartilage samples tested in PBS recorded an $<\mu s>$ of just 0.014 and an $<\mu k>$ of 0.008, levels similar to the HA bath (FIGS. 5b,c). Normal cartilage treated with HA-binding coatings and pre-incubated in HA was able to replicate the low friction characteristics of native cartilage tested in an HA-rich environment. This pivotal result suggests that most of the lubrication effects of HA on the tissue can be replicated by surface-bound HA alone, without the need for large concentrations of HA in the local environment. HABpep technology consistently reduced total friction values which include physiologically relevant and reproducible elements of interstitial fluid depressurization and boundary layer lubrication mechanisms (data not shown).

Example 5

Viscosupplementation of synovial fluid has long been hampered by inadequate residence time of the injected HA and poor targeting to the articular surface. The low levels of nonspecific binding between unmodified articular cartilage and HA suggests that absent a targeting factor, intra-articular injection of HA is unlikely to have a long-lasting effect on boundary lubrication. In the healthy knee, lubricin and other molecules are involved in targeting HA presentation to the articular surface. Furthermore, recent work suggests that HA binds to surface-attached lubricin molecules. The OA knee, in contrast, has a disrupted, fibrillated surface, and significantly lower levels of boundary lubricants. Coating the articular surface with synthetic HA binding functionalities may be able to concentrate scarce lubricants where they are most needed in order to improve disrupted boundary lubrication and decrease the rate of joint degeneration. The synthetic components of the coating are likely subject to slower turnover in vivo compared to HA; thus, removed or degraded HA could be continually replenished by this novel surface for far longer than HA injections alone.

Example 6

Figure 6:
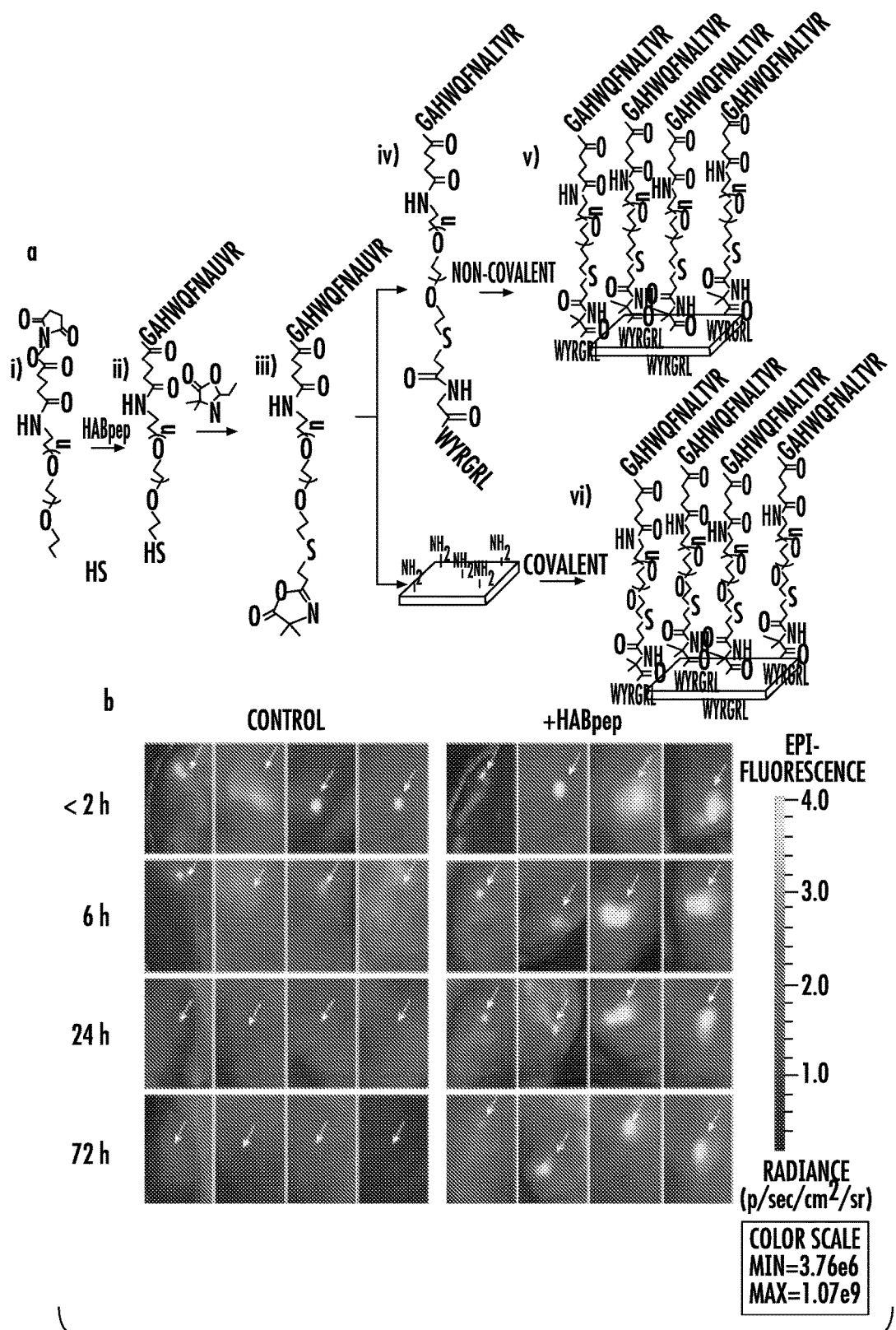
FIG. 6 depicts alternative embodiments for a single-step strategy for application of HABpep-polymer system to a tissue surface and functional translation to a joint environment. 6a, Schematic of synthesis of a PEG bifunctional linker with one end group as an HABpep (GAHWQFNALTVR) (SEQ ID NO: 10) and another end that either reacts with the amine groups or binds to a tissue surface via an extracellular matrix (ECM) binding peptide, such as collagen II binding peptide, WYRGRL (SEQ ID NO: 4). First, an HA-binding peptide is linked to a thiol-PEG-SGA linker (i) via amine-SGA conjugation reaction (ii) followed by the Michael-addition reaction of thiol functionality and vinyl dimethyl azlactone (iii). On a tissue surface, this amine-reactive azlactone functionality can be conjugated with either a peptide (iv) that non-covalently binds to ECM components (v), or covalently reacts with the amine functionality present in the tissue (vi). Both (iii) and (iv), with or without HA, can be applied on a tissue surface in a single-step application. 6b, HA-rhodamine together with HABpep-PEG-Col IIBpep polymer was injected into healthy rat knees in a single step and HA retention was monitored over time using an IVIS spectrum in vivo imager. HA-rhodamine (white arrows) via the HABpep polymer system was retained in rat knees even 72 hours post-injection, compared to only 6 hours without HABpep coating.

In further experiments, we applied the HABpep polymer to rat joints to evaluate in vivo efficacy of HA binding and retention in a complex environment. In a single step, a mixture of HABpep polymer (50 µL) designed to target Type II collagen (10.0 mg/mL) and fluorescently labeled HA (20.0 mg/mL) was injected into rat knees. Time course imaging of fluorescence demonstrated that the HABpep-polymer coating improved HA retention in rat joints compared to controls with no surface modification. Surface treatment in combination with the HA injection increased longevity of linear HA in the joint over 12-fold (6 hours in controls to 72 hours in surface treated joints, FIG. 6b). Through specific, non-covalent interactions, the HA was anchored to the tissue surfaces of the rat knee via Col IIBpep and the HABpep bridge. While lubricin is present in the normal joints tested, these in vivo experiments (FIG. 6b) demonstrated that bound HA via HABpep was retained for longer times in normal rat knees (up to 72 hours) compared to control without HABpep (6 hours). Therefore even in the complex and harsh environment of the knee, the polymer-peptide binding system increased retention of linear HA in the joint, prolonging the potential physical and biological benefits.

Example 7

Figure 7:
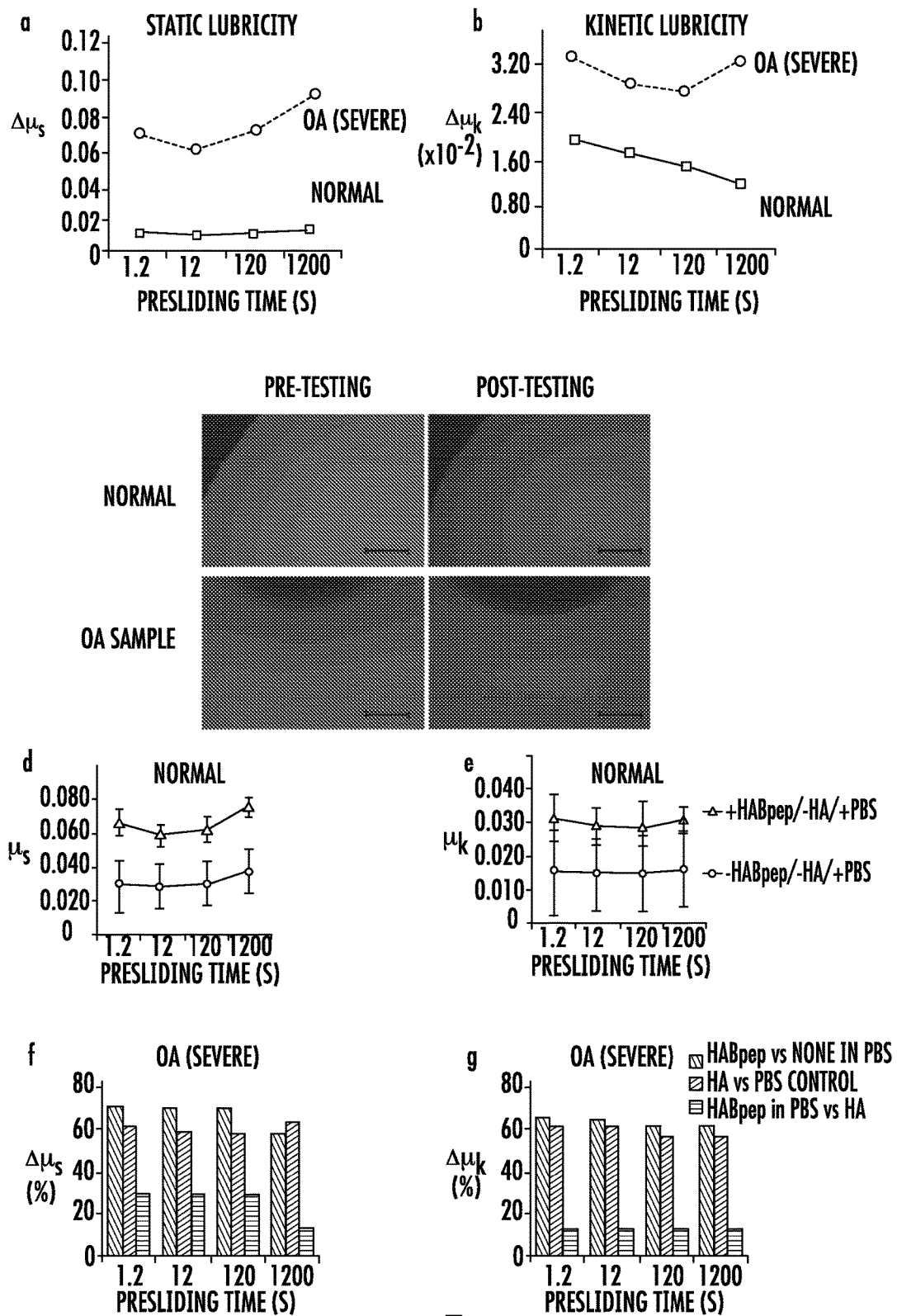
FIG. 7 depicts tissue surface modification with an HABpep-polymer system. 7a & b, Comparison of static and kinetic lubricity values ($<\mu>_{PBS}-<\mu>_{HA}$) of normal and severe OA samples coated with HABpep. 7c, Fluorescence microscope images of the normal and severe OA cartilage samples before and after tribological testing with HABpep coating and HA-rhodamine (scale bar=500 μm). 7d & e, Representative graphs of static friction and kinetic friction vs. pre-sliding time (s) for the normal cartilage sample in PBS with and without coating of HABpep. The resulting lubrication had a $\mu_s$ of 0.028-0.036 vs. 0.064-0.068 and a $\mu_k$ of 0.014-0.016 vs. 0.030-0.032, suggesting that the surface modification without HA resisted the surface movement. Percentage reduction of static friction and kinetic friction values with pre-sliding time (s) for cartilage samples at OA stage 3-4 (7f & g).
Figure 8:
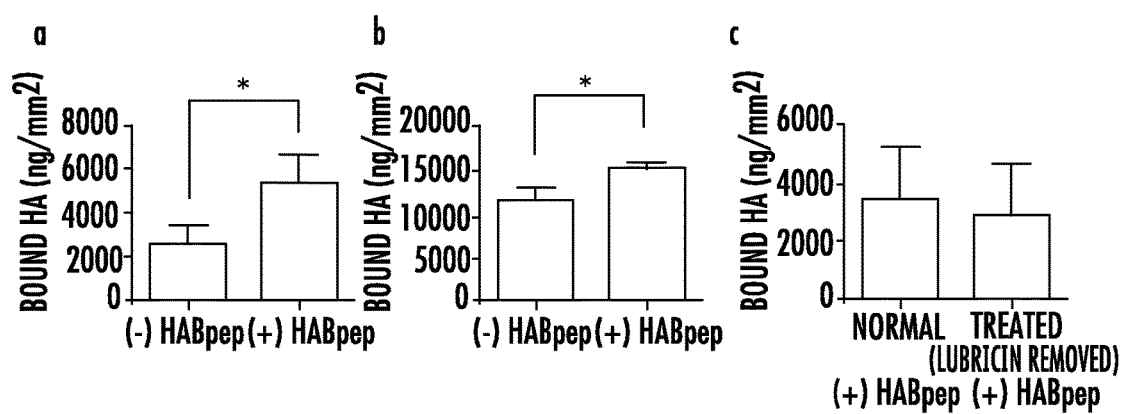
FIG. 8 depicts quantity of bound HA via HABpep on human normal cartilage and on cartilage treated to remove lubricin. Fluorescence studies were performed to calculate the amount of bound HA (ng/mm$^2$) with HABpep treatment or no HABpep treatment on native cartilage samples and cartilage samples treated to remove lubricin (n=5). 8a, Semi-quantitative analysis of fluorescence study showed 2.2 times more bound HA on native cartilage samples via HABpep treatment than the samples with no HABpep treatment. 8b, Cartilage samples that were treated to remove lubricin bound 1.3 times more HA via HABpep than the samples with no HABpep treatment. 8c, The bound HA due to HABpep treatment on both native cartilage and treated cartilage samples to remove lubricin remained unchanged.

Similar to the results from the normal cartilage surfaces, the OA cartilage samples treated with HABpep polymer coating that produces surface-bound HA produced static and kinetic friction values nearly equal to those found with testing in an HA bath (FIGS. 5d,e). OA cartilage samples with the HABpep polymer coating and bound HA had higher static and kinetic lubricity values compared to normal modified tissue (FIGS. 7a,b), which suggest that the HABpep and bound HA have a greater effect on improving the lubrication of rough OA surface compared to their effect in normal tissues. The practical implication is that even in a pathological environment, where low HA levels are present in the synovial fluid, the HA-binding coating can concentrate the limited HA available at the tissue surface to improve lubrication. Both normal and arthritic cartilage tissue benefited from application of the HA binding technology with respect to lubrication and HA retention in the articular joint, suggesting that the technology is useful even in the presence of lubricin or could be synergistically applied with lubricin. To further evaluate functional capabilities, the HA-binding technology was applied to normal and arthritic cartilage tissues that were treated to remove lubricin. Surface-bound HA via the HABpep-polymer coating system significantly reduced friction on normal ($<\mu s>$ of 0.23 to 0.12 and $<\mu k>$ of 0.12 to 0.047) and OA tissue ($<\mu s>$ of 0.24 to 0.13 and $<\mu k>$ of 0.12 to 0.051) confirming that the technology functions both in the presence and absence of lubricin (FIGS. 5f-i). As HA bound to the tissue surface coating was washed vigorously before testing (FIG. 4a), the improved lubrication implies that a relatively stable surface coating of HA is generated on the tissue that will not be quickly flushed from the joint. Fluorescence imaging of the cartilage explants pre- and post-mechanical testing also verified the retention of HA-rhodamine onto the surface (FIG. 7c). Semi-quantitative analysis of surface fluorescence found that HABpep increased binding of HA compared to no treatment. HABpep increased surface binding on normal tissue and tissue treated to remove lubricin (FIG. 8). Prophylactic treatment with HA-binding coatings during trauma treatment may also be able to enhance local surface lubrication and prevent or reduce the onset of joint degeneration.

Example 8

Figure 9:
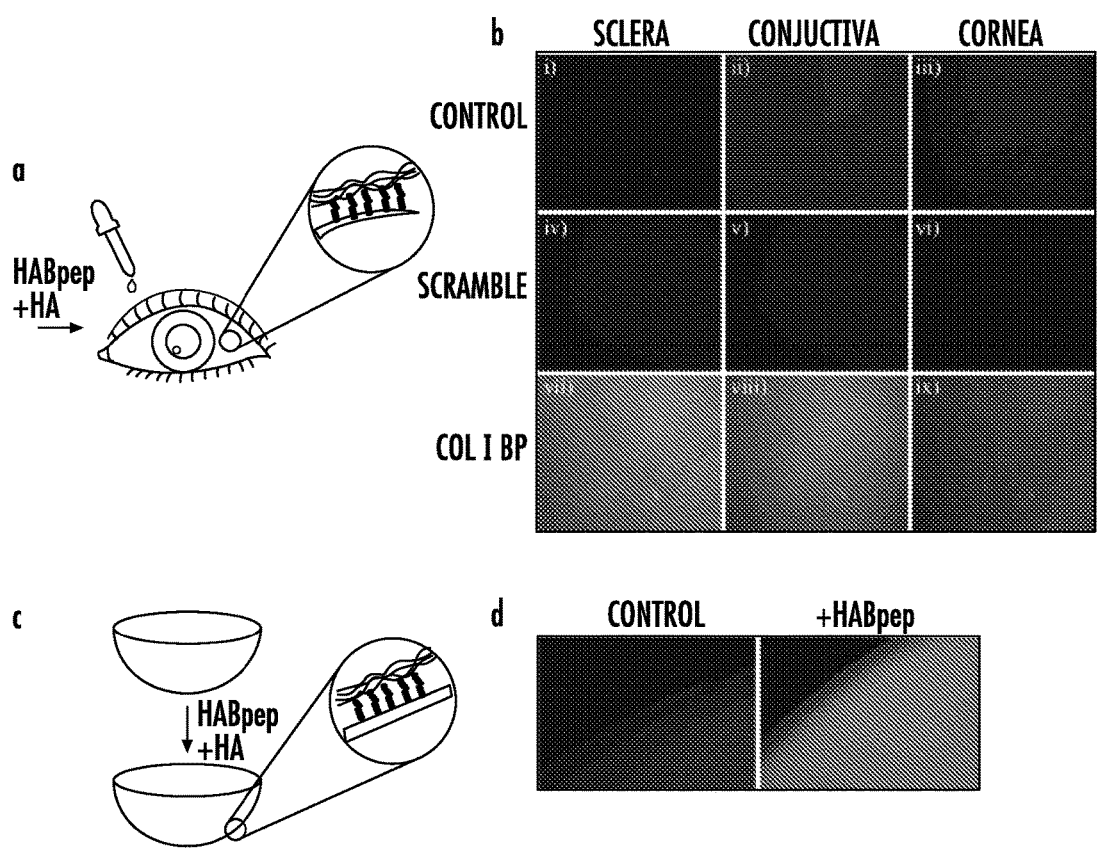
FIG. 9 shows an ocular surface embodiment of HABpep-polymer system. 9a, HABpep polymer system as an eyedrop solution can be used to retain HA on the eye surface. Collagen I-abundant eye tissues without epithelial layers, such as sclera, conjunctiva and cornea, act as anchors for the HABpep polymer system. 9b, Fluorescence images of HA retention on untreated and treated eye tissues: sclera, conjunctiva and cornea of untreated eye, i) to iii); treated with scrambled collagen I binding peptide (YFDEYSLSQS), iv) to vi); and treated with collagen I binding peptide, vii to ix). 9c, Contact lens modification with the HABpep polymer system was performed by the covalent reaction methodology. 9d, Fluorescence images for HA-rhodamine retention on modified contact lens showed relatively darker staining compared to the control.

HA is a key molecule in many tissues and its therapeutic application is extending to other fields, including ophthalmology. HA is an important component of artificial tears to treat dry eye and in eye drops that accelerate healing after surgery or trauma. Many ophthalmic products, including multipurpose contact lens care solutions take advantage of HA's ability to enhance wettability and water retention, which is much needed in treating dry eye disorders. Furthermore, HA provides several biological benefits to ocular tissues, such as improving corneal epithelial cell migration and wound healing, reducing inflammation and protecting cells from free-radical damage. Therefore, we investigated the application of the HA-binding strategy to ocular tissues, such as sclera, conjunctiva and cornea of an eye, and to medical devices, such as contact lenses. We applied HA bound to HABpep polymer as an eye-drop with the polymer-peptide system anchored onto Type I collagen of the sclera, conjunctiva and cornea of an eye via collagen I binding peptide (FIG. 9a). Fluorescently labeled HA exposed to the treated ocular surface tissues demonstrated stronger binding compared to a scrambled peptide and control untreated tissues, with the sclera showing the highest levels of binding (FIG. 9b). This eye-drop methodology can recruit and retain HA via HABpep functionalization on eye surfaces with a damaged epithelial layer. Extending the technology to a synthetic device, a contact lens surface was covalently modified with the HABpep polymer system (FIG. 9c). Fluorescently labeled HA via HABpep was visualized bound to the lens, confirming the presence of the surface coating (FIG. 9d). As a functional test for HA binding on contact lenses, the rate of water evaporation from lenses was evaluated. The water evaporation rate decreased significantly on the coated contact lens (0.23±0.026 µL/min) compared to a bare contact lens (0.50±0.017 µL/min) and a control contact lens with only physically adsorbed HA (0.39±0.033 µL/min).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A biomaterial comprising at least one biologically compatible polymer having one or more hyaluronic acid (HA) binding peptides (HABPep) selected from the group consisting of: RRDDGAHWQFNALTVR (SEQ ID NO: 1), CRRDDGAHWQFNALTVR (SEQ ID NO: 2) or a conservative amino acid substitution thereof at a residue position other than 4, 5, 6, 9, 10 or 11, GAAWQFNALTVR (SEQ ID NO: 9) or a conservative amino acid substitution thereof at a residue position other than 4, 5, 6, 9, 10 or 11, GAHWQFAALTVR (SEQ ID NO: 10) or a conservative amino acid substitution thereof at a residue position other than 4, 5, 6, 9, 10 or 11, and iv) GAHWQFNALTVA (SEQ ID NO: 11) or a conservative amino acid substitution thereof at a residue position other than 4, 5, 6, 9, 10 or 11, covalently linked to the biologically compatible polymer, and one or more extracellular matrix binding peptides (ECMBPep) covalently linked to the biologically compatible polymer.

2. The biomaterial of claim 1, further comprising HA bound to the HABPep.

3. The biomaterial of claim 1, wherein the ECMBpep is selected from the group consisting of YSFYSDESLQ (SEQ ID NO: 3) and WYRGRL (SEQ ID NO: 4).

4. The biomaterial of claim 3, wherein the biocompatible polymer is hydrophilic.

5. The biomaterial of claim 3, wherein the biocompatible polymer is selected from the group consisting of: Poly(ethylene glycol), Poly(propylene glycol), Poly(methyl vinyl ether), Oligoethylene, Poly(isobutylene) Poly(tetrahydrofuran) Poly(oxytrimethylene), Poly(dimethylsiloxsane), Poly(dimethylsilane), Nylon 6, Nylon 11, Poly(acrylonitrile), Squalane, Poly(1,3-dioxolane), Poly(iminooligomethylene), Poly(l-lysine), Polyethyleneimine, Poly(adipate), Poly(l-caprolactone), Poly(L-lactic acid), or derivatives thereof.

6. The biomaterial of claim 3, wherein the one or more biocompatible polymers are mono, disubstituted, or multi-substituted with at least one functional group.

7. A method of coating a tissue with the biomaterial of claim 3, comprising contacting the tissue with the biomaterial.

8. A method for making the biomaterial of claim 1, comprising:
   a) obtaining a sufficient amount of one or more biocompatible polymers conjugated to at least one or more N-succinimide groups and one or more maleimide groups in a suitable solution;
   b) adding to the solution of a) a sufficient amount of one or more ECMBPep and allowing it to react with the one or more N-succinimide groups to produce one or more biocompatible polymers having one or more ECMB-Pep which are covalently linked to the biocompatible polymers;
   c) obtaining a sufficient amount of having one or more thiolated hyaluronic acid (HA) binding peptides selected from the group consisting of: RRDDGAHWQFNALTVR (SEQ ID NO: 1), CRRDDGAHWQF-NALTVR (SEQ ID NO: 2) or a conservative amino acid substitution thereof at a residue position other than 4, 5, 6, 9, 10 or 11, GAAWQFNALTVR (SEQ ID NO: 9) or a conservative amino acid substitution thereof at a residue position other than 4, 5, 6, 9, 10 or 11, GAHWQFAALTVR (SEQ ID NO: 10) or a conservative amino acid substitution thereof at a residue position other than 4, 5, 6, 9, 10 or 11, and iv) GAHWQF-NALTVA (SEQ ID NO: 11) or a conservative amino acid substitution thereof at a residue position other than 4, 5, 6, 9, 10 or 11, (C-HABPep) in a suitable solution;
   d) adding the solution of b) to the solution of c) and mixing for a sufficient period of time to produce one or more biocompatible polymers having one or more HA binding peptides (HABPep) selected from the group consisting of: RRDDGAHWQFNALTVR (SEQ ID NO: 1), CRRDDGAHWQFNALTVR (SEQ ID NO: 2) or a conservative amino acid substitution thereof at a residue position other than 4, 5, 6, 9, 10 or 11, GAAWQFNALTVR (SEQ ID NO: 0.9) or a conservative amino acid substitution thereof at a residue position other than 4, 5, 6, 9, 10 or 11, GAHWQFAALTVR (SEQ ID NO: 10) or a conservative amino acid substitution thereof at a residue position other than 4, 5, 6, 9, 10 or 11, and iv) GAHWQFNALTVA (SEQ ID NO: 11) or a conservative amino acid substitution thereof at a residue position other than 4, 5, 6, 9, 10 or 11, which are covalently linked to the biocompatible polymers which are covalently linked to one or more ECMBPep;
   e) adding to the solution of d) a sufficient amount of hyaluronic acid (HA) in a suitable solvent for a sufficient time to allow HA to bind to the HABPep in the solution;
   f) removing the unreacted reagents of b), c) and e) and purifying the remaining product.

9. The method of claim 8, wherein the one or more biocompatible polymers is Poly(ethylene glycol).

10. A method for treating a cartilage defect in a tissue of a subject comprising administering to the cartilage defect in the subject in need of treatment an effective amount of the biomaterial composition of claim 1.

11. A method for treating osteoarthritis in the tissues of a subject comprising administering to the tissues in the subject in need of treatment an effective amount of the biomaterial composition of claim 1.

12. The method of claim 10, wherein the biomaterial composition further comprises an additional therapeutic agent.

13. The method of claim 10, wherein the biomaterial is administered together with hyaluronic acid (HA) in one step.

* * * * *

SEQUENCE LISTING

```
<160> NUMBER OF SEQ ID NOS: 11

<210> SEQ ID NO 1
<211> LENGTH: 16
<212> TYPE: PRT
<213> ORGANISM: Homo sapiens

<400> SEQUENCE: 1

Arg Arg Asp Asp Gly Ala His Trp Gln Phe Asn Ala Leu Thr Val Arg
1               5                   10                  15

<210> SEQ ID NO 2
<211> LENGTH: 17
<212> TYPE: PRT
<213> ORGANISM: Homo sapiens

<400> SEQUENCE: 2

Cys Arg Arg Asp Asp Gly Ala His Trp Gln Phe Asn Ala Leu Thr Val
1               5                   10                  15

Arg

<210> SEQ ID NO 3
<211> LENGTH: 10
<212> TYPE: PRT
<213> ORGANISM: Homo sapiens
```

<400> SEQUENCE: 3

Tyr Ser Phe Tyr Ser Asp Glu Ser Leu Gln
1               5                   10

<210> SEQ ID NO 4
<211> LENGTH: 6
<212> TYPE: PRT
<213> ORGANISM: Homo sapiens

<400> SEQUENCE: 4

Trp Tyr Arg Gly Arg Leu
1               5

<210> SEQ ID NO 5
<211> LENGTH: 10
<212> TYPE: PRT
<213> ORGANISM: Homo sapiens

<400> SEQUENCE: 5

Tyr Phe Asp Glu Tyr Ser Leu Ser Gln Ser
1               5                   10

<210> SEQ ID NO 6
<211> LENGTH: 6
<212> TYPE: PRT
<213> ORGANISM: Homo sapiens

<400> SEQUENCE: 6

Tyr Arg Leu Gly Arg Trp
1               5

<210> SEQ ID NO 7
<211> LENGTH: 9
<212> TYPE: PRT
<213> ORGANISM: Homo sapiens

<400> SEQUENCE: 7

Gln Phe Tyr Asp Thr Arg Thr Ser Glu
1               5

<210> SEQ ID NO 8
<211> LENGTH: 9
<212> TYPE: PRT
<213> ORGANISM: Homo sapiens

<400> SEQUENCE: 8

Gln Asp Ser Glu Thr Arg Thr Phe Tyr
1               5

<210> SEQ ID NO 9
<211> LENGTH: 12
<212> TYPE: PRT
<213> ORGANISM: Homo sapiens

<400> SEQUENCE: 9

Gly Ala Ala Trp Gln Phe Asn Ala Leu Thr Val Arg
1               5                   10

<210> SEQ ID NO 10
<211> LENGTH: 12
<212> TYPE: PRT
<213> ORGANISM: Homo sapiens

<400> SEQUENCE: 10

```
Gly Ala His Trp Gln Phe Ala Ala Leu Thr Val Arg
1               5                   10

<210> SEQ ID NO 11
<211> LENGTH: 12
<212> TYPE: PRT
<213> ORGANISM: Homo sapiens

<400> SEQUENCE: 11

Gly Ala His Trp Gln Phe Asn Ala Leu Thr Val Ala
1               5                   10
```